US008706206B2

(12) United States Patent
Kanai et al.

(10) Patent No.: US 8,706,206 B2
(45) Date of Patent: Apr. 22, 2014

(54) HUMAN FATIGUE ASSESSMENT DEVICE AND HUMAN FATIGUE ASSESSMENT METHOD

(75) Inventors: Etsuko Kanai, Kyoto (JP); Masami Funakura, Osaka (JP); Yasuyoshi Watanabe, Hyogo (JP); Masaaki Tanaka, Osaka (JP); Yoshihito Shigihara, Osaka (JP); Kei Mizuno, Hyogo (JP)

(73) Assignee: Panasonic Corporation, Osaka (JP)

( * ) Notice: Subject to any disclaimer, the term of this patent is extended or adjusted under 35 U.S.C. 154(b) by 323 days.

(21) Appl. No.: 13/142,604

(22) PCT Filed: Oct. 26, 2010

(86) PCT No.: PCT/JP2010/006309
§ 371 (c)(1),
(2), (4) Date: Jun. 29, 2011

(87) PCT Pub. No.: WO2011/052183
PCT Pub. Date: May 5, 2011

(65) Prior Publication Data
US 2011/0288424 A1    Nov. 24, 2011

(30) Foreign Application Priority Data

Oct. 29, 2009  (JP) .................................. 2009-249537

(51) Int. Cl.
*A61B 5/04*     (2006.01)
*A61B 5/02*     (2006.01)

(52) U.S. Cl.
USPC ......................................... 600/544; 600/500

(58) Field of Classification Search
USPC ................................. 600/500–507, 544–545
See application file for complete search history.

(56) References Cited

U.S. PATENT DOCUMENTS

2006/0247542 A1*  11/2006  Watanabe et al. ............. 600/500
2007/0021673 A1*   1/2007  Arbel et al. .................... 600/500
(Continued)

FOREIGN PATENT DOCUMENTS

JP       08-089488      4/1996
JP       11-155845      6/1999
(Continued)

OTHER PUBLICATIONS

Noda, et al. "Change of EEG, HRV, and psychological arousal level and hedonic tone in finger movement." Research Journal of Sport Science in Nara Women's University. Mar. 2009. vol. 11. pp. 1-14.*

(Continued)

*Primary Examiner* — Patricia Mallari
*Assistant Examiner* — Tiffany Weston
(74) *Attorney, Agent, or Firm* — Wenderoth, Lind & Ponack, L.L.P.

(57) ABSTRACT

A human fatigue assessment device capable of performing highly accurate fatigue assessment is provided. The human fatigue assessment device includes: a physiological signal measuring unit which measures a pulse wave signal of a user; a feature value extracting unit which extracts first feature values each of which is obtained from a systolic posterior component of the pulse wave signal measured by the physiological signal measuring unit; a storage unit in which the first feature values extracted by the feature value extracting unit are stored; and a fatigue determining unit which determines whether or not the user is fatigued, using the first feature values extracted by the feature value extracting unit, in which the fatigue determining unit compares a first feature value among the first feature values extracted by the feature value extracting unit and at least one of the first feature values stored in the storage unit, to determine whether or not the user is fatigued.

10 Claims, 27 Drawing Sheets

(56) References Cited

U.S. PATENT DOCUMENTS

| | | | |
|---|---|---|---|
| 2009/0198147 A1* | 8/2009 | Ono et al. | 600/554 |
| 2010/0179441 A1 | 7/2010 | Kanai et al. | |
| 2010/0217137 A1* | 8/2010 | Kanai et al. | 600/500 |

FOREIGN PATENT DOCUMENTS

| | | | | |
|---|---|---|---|---|
| JP | 2005-028016 | | 2/2005 | |
| JP | 2005-329148 | | 12/2005 | |
| JP | 3790266 | | 6/2006 | |
| JP | 2008-125801 | | 6/2008 | |
| JP | 2009-022610 | | 2/2009 | |
| JP | 2009-178456 | | 8/2009 | |
| WO | WO 2004/028362 | * | 4/2004 | A61B 5/04 |
| WO | 2005/000119 | | 1/2005 | |
| WO | WO 2008/149559 | * | 11/2008 | A61B 5/16 |
| WO | 2008/149559 | | 12/2008 | |

OTHER PUBLICATIONS

Lal et al. "A critical review of the psychophysiology of driver fatigue." Biological Psychology. 2001. pp. 173-194.*

Jap et al. "Using EEG spectral components to assess algorithms for detecting fatigue." Expert Systems with Applications. Mar. 2009. pp. 2352-2359.*

International Search Report issued Dec. 7, 2010 in International (PCT) Application No. PCT/JP2010/006309.

Satomi Noda et al., "Teyubi no Undo o Tomonau Asobi ni Okeru Noha•Jiritsu Shinkei Kino Shihyo Oyobi Shinriteki Kakuseido•Kaikando no Henka" ("change of EEG, HRV and psychological arousal level and hedonic tone in finger movement"), Research Journal of Sport Science in Nara Women's University, Mar. 31, 2009, vol. 11, pp. 21 to 26.

G. Mulder. L. J. M. Mulder, Information Processing and Cardiovascular Control, Psychophysiology, Jul. 1981, vol. 18, Issue 4, pp. 392-402.

Satomi Noda et al., "Changes in EGG and psychological arousal level and hedonic tone level during a finger movement", Japanese Journal of Biofeedback Research, Apr. 25, 2009, vol. 36, No. 1, pp. 41 and 43 to 46.

Yoshihito Shigihara et al., "Jidosha Unten o Sotei Shita Kyusei Seishin Hiro no Kyakkanteki Hyokakei no Kakuritsu". Nippon Hiro Gakkaishi, Jun. 25, 2010, vol. 6, No. 1, p. 51.

Kaida K et al., Validation of the Karolinska sleepiness scale against performance and EEG variables. Clinical Neurophysiology 117: 1574-1581, May 6, 2006.

Akiko Suzuki et al .. "Work Efficiency and Physiological Responses With the Use of a Thimble in Skilled and Unskilled Sewers Respiratory Activities and EEG", Japanese Journal of physiological anthropology, Aug. 25, 2000, vol. 5, No. 3, pp. 7 to 14.

* cited by examiner

P1: Ejection wave
P2: Reflection wave
(1): Systolic posterior component

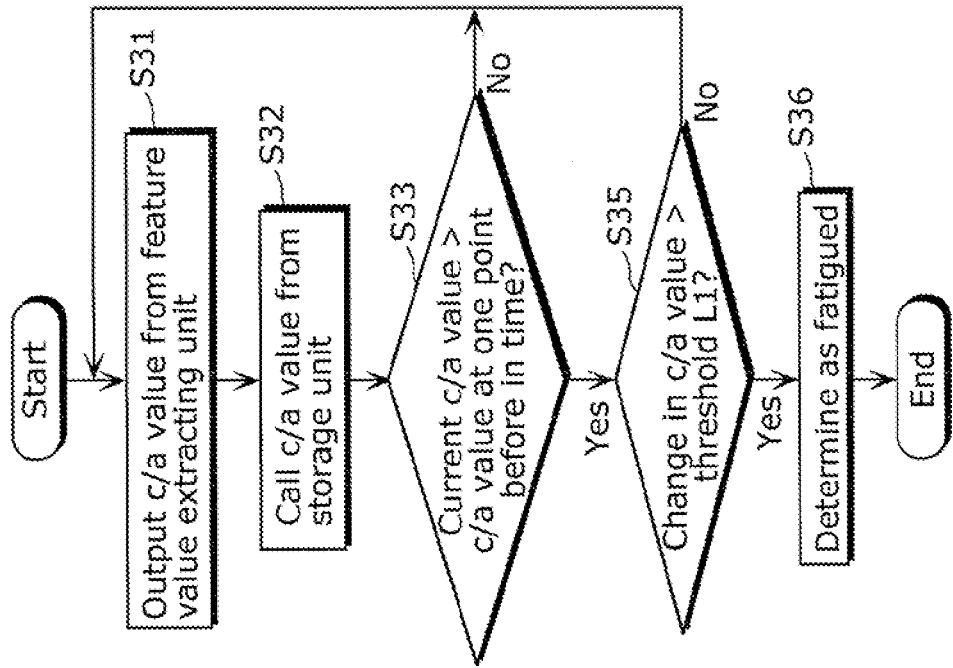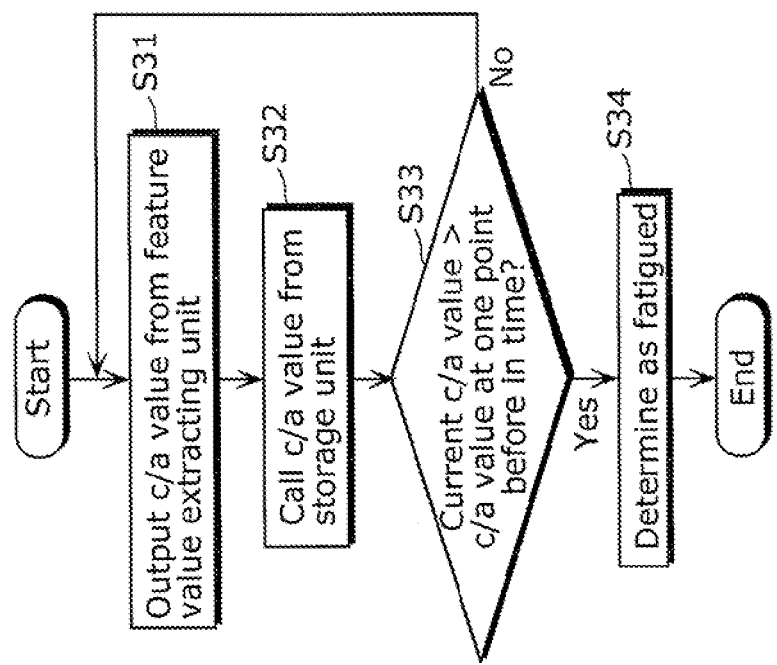

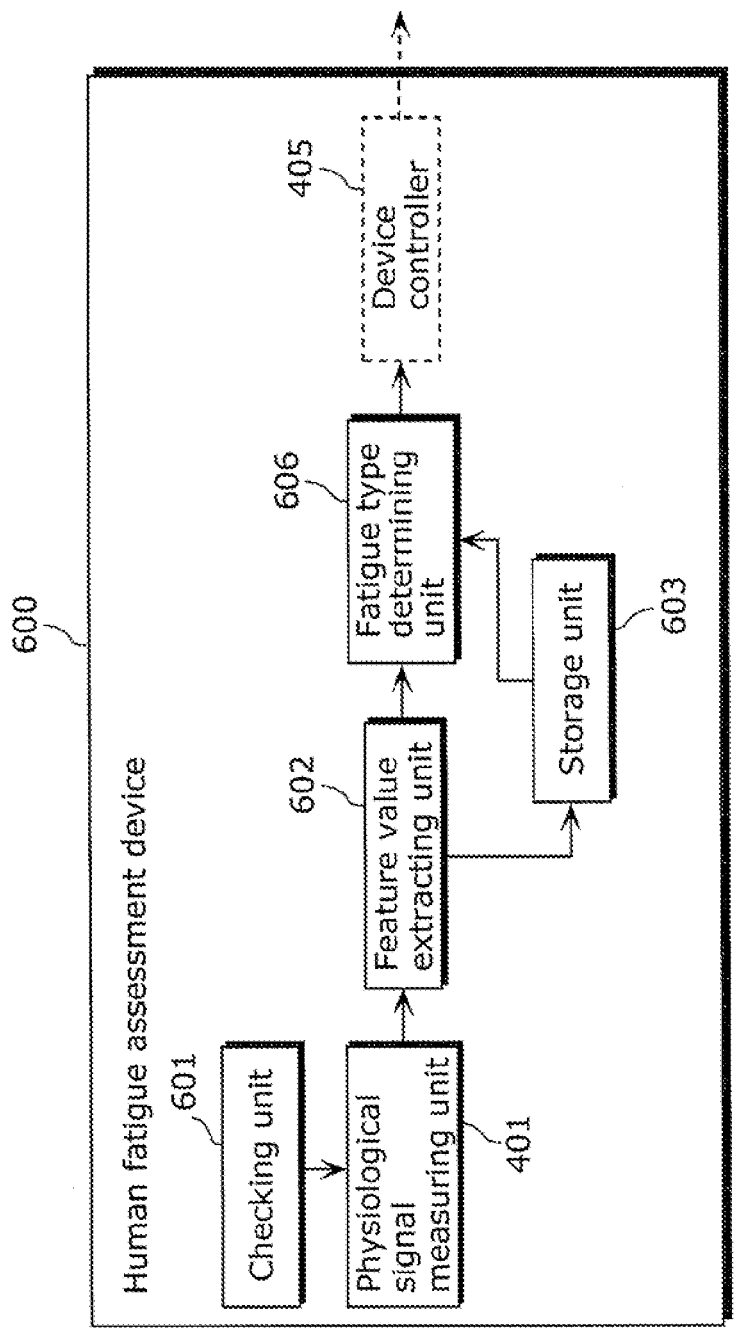

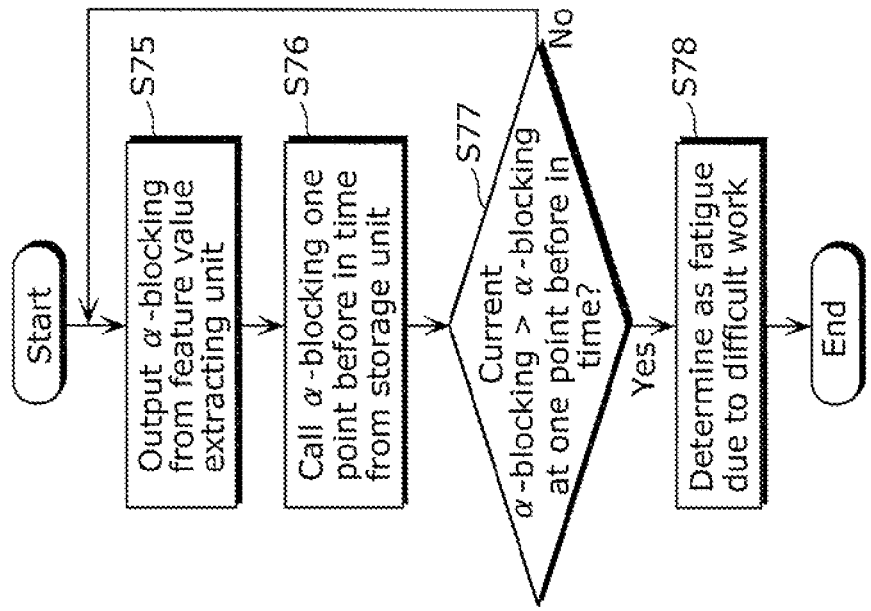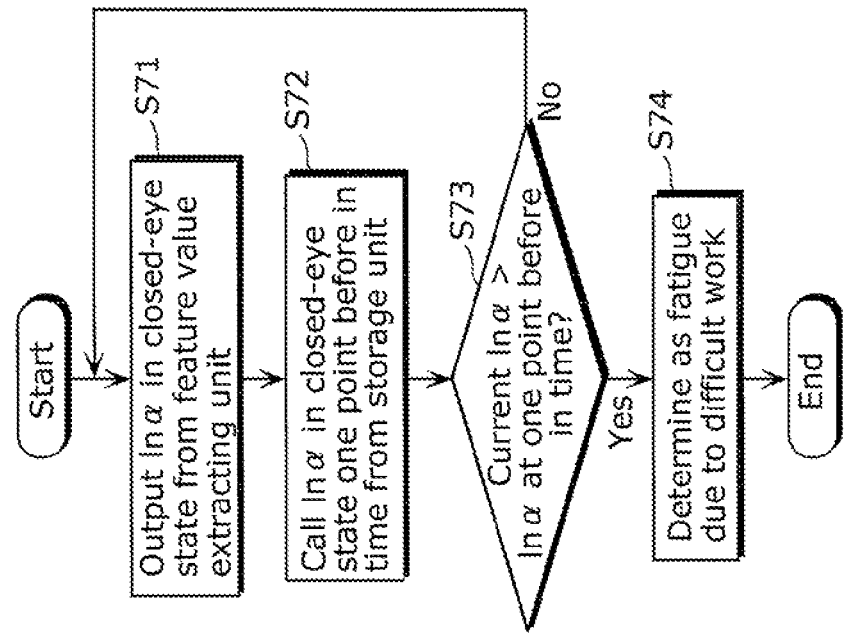

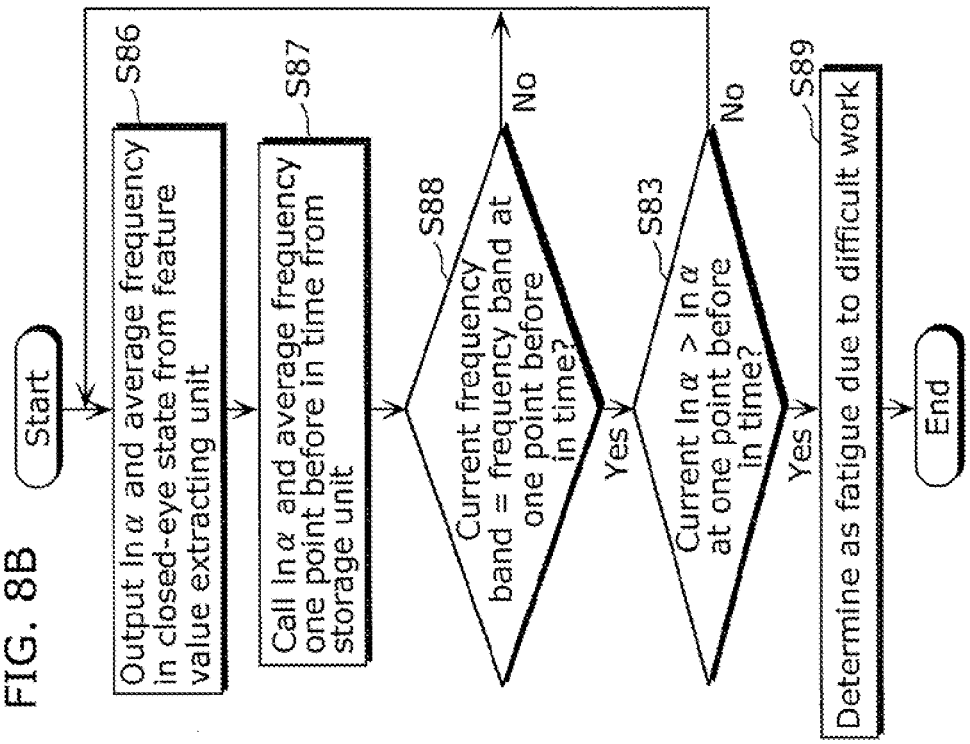
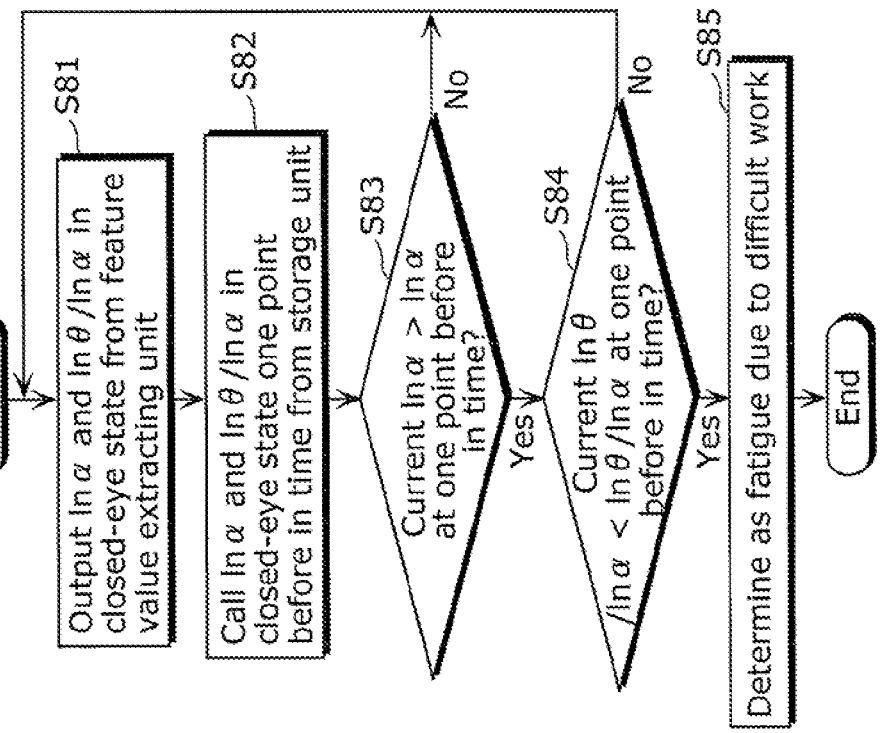

FIG. 15A

|  |  | Total fatigue VAS | Mental fatigue VAS |
|---|---|---|---|
| 0-back | Mean | 44.61 | 40.86 |
|  | SD | 17.37 | 17.04 |
|  | Mean | 49.81 | 47.11 |
|  | SD | 20.54 | 20.24 |
|  | Before and after P value | 0.024 | 0.043 |
| 2-back | Mean | 45.50 | 43.56 |
|  | SD | 15.75 | 13.25 |
|  | Mean | 50.06 | 49.94 |
|  | SD | 19.55 | 18.23 |
|  | Before and after P value | 0.049 | 0.034 |

FIG. 15B

| n-back | 0-back | 2-back | P value |
|---|---|---|---|
| Total fatigue VAS | 43.9 ± 20.6 | 51.8 ± 21.5 | 0.083 |
| Mental fatigue VAS | 44.0 ± 20.7 | 53.8 ± 19.8 | 0.048 |
| Physical fatigue VAS | 42.0 ± 17.1 | 48.7 ± 20.9 | 0.053 |
| Stress VAS | 46.4 ± 17.5 | 50.9 ± 22.6 | 0.328 |
| Motivation VAS | 41.9 ± 17.2 | 41.3 ± 20.4 | 0.863 |
| Sleepiness VAS | 46.2 ± 23.7 | 40.2 ± 24.5 | 0.311 |
| Difficulty VAS | 24.7 ± 18.3 | 53.4 ± 20.2 | 0.000 |
| Monotonousness VAS | 66.8 ± 20.3 | 42.7 ± 22.4 | 0.002 |
| Boredom VAS | 63.9 ± 19.1 | 44.8 ± 23.9 | 0.023 |
| Drowsiness KSS | 6.2 ± 1.8 | 4.6 ± 2.2 | 0.008 |

2-back test significantly higher 0-back test significantly higher

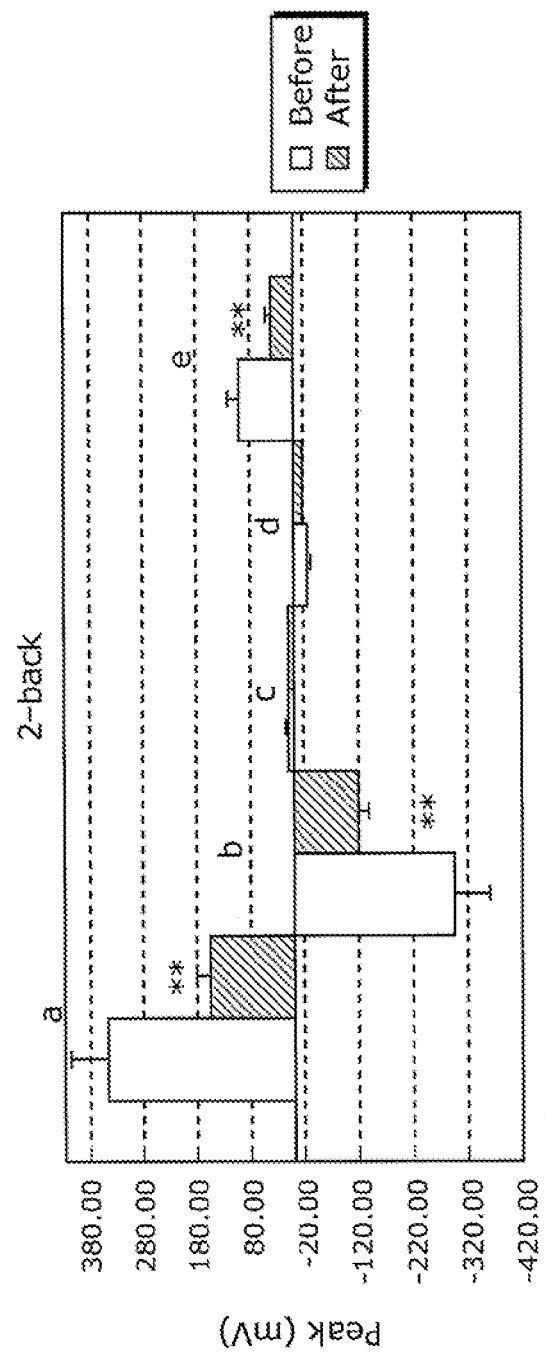

Values are indicated in mean values and standard errors **P < 0.05

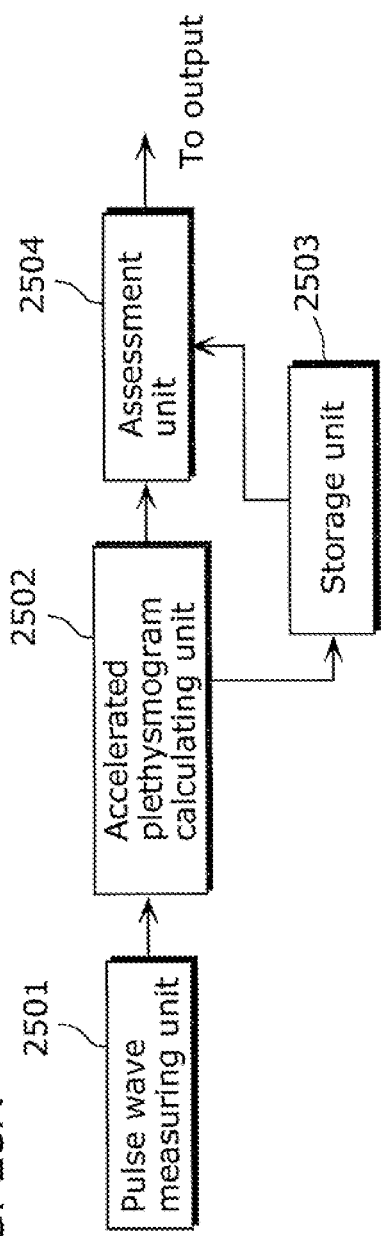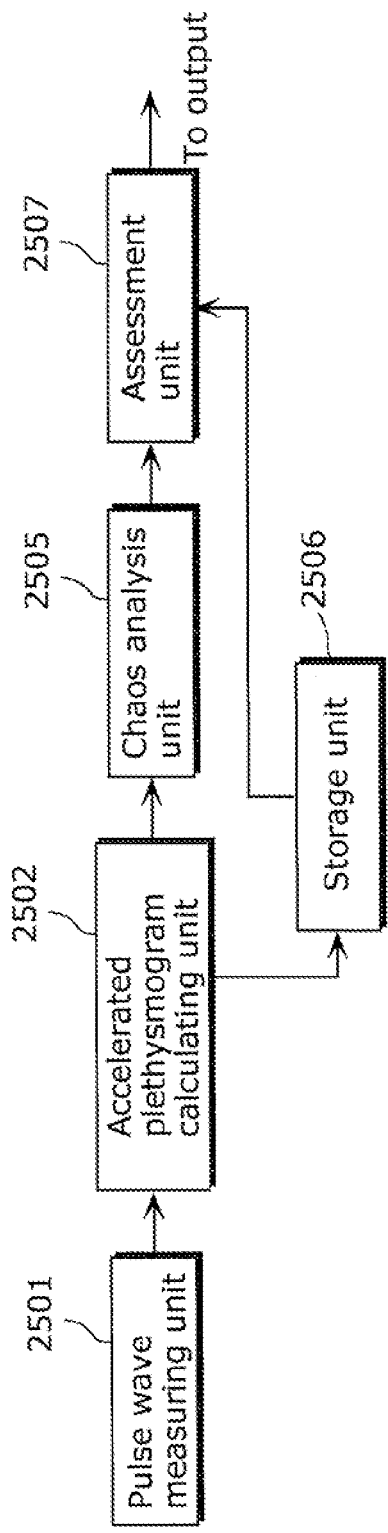

HUMAN FATIGUE ASSESSMENT DEVICE AND HUMAN FATIGUE ASSESSMENT METHOD

TECHNICAL FIELD

The present invention relates to a human fatigue assessment device and a human fatigue assessment method which assess fatigued state of human from physiological signals.

BACKGROUND ART

In recent years, experts have been emphasizing importance of objective assessment of human fatigue for preventing deaths caused by accidents and overwork in the automotive and occupational fields. Upon assessing such fatigue, it is important to make the assessment in real time in practical situations, and to notify the user to pay attention to his fatigue, instead of the conventional fatigue assessments made in laboratories. However, the conventional assessments methods were not non-invasive, non-restraint, or simple, making the methods difficult to use in practical assessments.

In response to this problem, a method of clarifying correlation between feature values obtained from human pulse wave signals and fatigue to assess fatigue from pulse waves as a human fatigue assessment device aiming for practical use (for example, see Patent Literature 1). FIGS. 25A and 25B are block diagrams illustrating configurations of conventional human fatigue assessment device according to Patent Literature 1. The device in Patent Literature 1 shall be described with reference to FIGS. 25A and 25B as follows.

As illustrated in FIG. 25A, when a pulse wave measuring unit 2501 measures a pulse wave signal, an accelerated plethysmogram calculating unit 2502 calculates accelerated plethysmogram from the measured pulse wave signal, extracts waveform component of the accelerated plethysmogram, and calculates peak values of the first wave (a wave) to the fifth wave (e wave). Next, an assessment unit 2504 assesses that the user is in fatigued state when the newly calculated peak value is small than a reference value of a peak value of the accelerated plethysmogram stored in a storage 2503. More specifically, Patent Literature 1 particularly focuses on the a wave among waveform components of the accelerated plethysmogram, and illustrates the correlation between a decrease in the reduced peak value of the a wave and fatigue.

Patent Literature 1 also discloses a configuration in which a chaos analysis unit 2505 is added between the accelerated plethysmogram calculating unit 2502 and an assessment unit 2507, as illustrated in FIG. 25B. The chaos analysis unit 2505 performs a chaos analysis on the accelerated plethysmogram calculated by the accelerated plethysmogram calculating unit 2502, and calculates a maximal Lyapunov exponent. Next, the assessment unit 2507 assesses that the user is in fatigued state when the newly calculated maximal Lyapunov exponent is smaller than a reference value of maximal Lyapunov exponent stored in the storage unit 2506. According to Patent Literature 1, the configuration described above allows a non-invasive assessment of fatigue.

In addition, a method of estimating a state of a user, such as tension or sleepiness based on activities in autonomic nerves calculated by using pulse information corresponding to heartbeat obtained by measuring a pulse wave signal of a driver through a pulse wave measuring unit embedded in a steering wheel and others (for example, see Patent Literature 2).

In the method proposed in Patent Literature 2, when the amount of sympathetic nerve activity increases and the amount of parasympathetic nerve activity decreases (that is, when the sympathetic nerves are dominant), the driver is determined to be "excited" including an irritated state or an excited state. Alternatively, when the amount of sympathetic nerve activity decreases and the amount of parasympathetic nerve increases (that is, when the parasympathetic nerves are dominant), the driver is determined to be "sleepy" including a very sleepy state or an exhausted state. Alternatively, when both the amount of sympathetic nerve activity and the amount of parasympathetic nerve activity increase, the driver is determined to be "sleepy (contradicting)" indicating that the driver is trying to overcome the sleepiness, and when both the amount of sympathetic nerve activity and the amount of parasympathetic nerve amount decrease, the driver is determined to be "depressed (contradicting)"; that is, in a depressed state.

CITATION LIST

Patent Literature

[Patent Literature 1] Japanese Patent No. 3790266
[Patent Literature 2] Japanese Unexamined Patent Application Publication No. 2008-125801

SUMMARY OF INVENTION

Technical Problem

However, the pulse waves vary due to influence other than fatigue. Thus, with the configuration illustrated in FIG. 25A, the measured values are not very reproducible, making it difficult to maintain accuracy of the assessment.

On the other hand, when performing a chaos analysis as illustrated in FIG. 25B, it is possible to reduce the influence other than fatigue. However, complex processing for chaos analysis increases the amount of calculation, and certain amount of data is necessary for the analysis. As a result, real-time analysis is difficult.

Furthermore, although Patent Literature 2 proposes an estimation by grouping the user's state in four states using pulse wave signals, no supporting data as to how the states are determined is not included. Thus, it is not clear whether or not the grouping is more than an arbitrary grouping.

The present invention has been conceived to solve these problems, and it is an object of the present invention to provide a human fatigue assessment device and a human fatigue assessment method capable of highly precise assessment on fatigue.

Solution to Problem

In order to solve the problems, the human fatigue assessment device according to an aspect of the present invention includes a human fatigue assessment device including: a physiological signal measuring unit which measures a pulse wave signal of a user; a feature value extracting unit which extracts first feature values each of which is obtained from a systolic posterior component of the pulse wave signal measured by the physiological signal measuring unit; a storage unit in which the first feature values extracted by the feature value extracting unit are stored; and a fatigue determining unit which determines whether or not the user is fatigued, using the first feature values extracted by the feature value extracting unit, in which the fatigue determining unit compares a first feature value among the first feature values extracted by the feature value extracting unit and at least one of the first feature values stored in the storage unit, to determine whether or not the user is fatigued.

With this configuration, the first feature values obtained from the systolic posterior component of the pulse wave signal are extracted, and whether the user is fatigued or not is determined by comparing a first feature value among the extracted first feature values and at least one of the first feature values stored in the storage unit. Here, although the systolic posterior component of the pulse wave signal is affected by factors other than fatigue, it is less susceptible to the influence of fatigue. Accordingly, using the first feature values obtained from the systolic posterior component reduces the influence due to the factors other than fatigue, improving the accuracy of the fatigue assessment.

In addition, it is preferable that the feature value extracting unit calculates an accelerated plethysmogram from the pulse wave signal, and extracts the first feature values, using information on at least a c wave or a d wave which is a component wave of an accelerated plethysmogram corresponding to the systolic posterior component.

Furthermore, this configuration reduces the influence of the factors other than fatigue compared to a case in which the fatigue is assessed based on the peak value of the accelerated plethysmogram waveform itself, and improves the accuracy of the fatigue assessment, by using the information on the c wave or the d wave.

In addition, it is preferable that the feature value extracting unit extracts a ratio of a peak value of the c wave with respect to a peak value of an a wave, a b wave, or an e wave in the accelerated plethysmogram as the first feature value, and the fatigue determining unit determines that the user is fatigued, when absolute values of the first feature values increase in time-series.

In addition, with this configuration using the ratio of the c wave with respect to the peak values of the a wave, the b wave, or the e wave improves the accuracy of the fatigue assessment by reducing the influence of the factors other than fatigue compared to a case in which the fatigue is assessed based on the peak value of the accelerated plethysmogram waveform itself.

In addition, it is preferable that the feature value extracting unit extracts a difference between peak values of the a wave and the c wave in the accelerated plethysmogram, and the fatigue determining unit determines that the user is fatigued when absolute values of the first feature values decrease in time-series.

Furthermore, this configuration using the difference between the peak value of the a wave and the peak value of the c wave reduces the influence of the factors other than fatigue compared to a case in which the fatigue is assessed based on the peak value of the accelerated plethysmogram waveform itself, and improves the accuracy of the fatigue assessment.

In addition, it is preferable that the feature value extracting unit extracts a value obtained by dividing a difference between peak values of the c wave and the d wave in the accelerated plethysmogram by the a wave in the accelerated plethysmogram, and the fatigue determining unit determines that the user is fatigued when absolute values of the first feature values increase in time-series.

Furthermore, this configuration using a value obtained by dividing the difference between the peak value of the c wave and the peak value of the d wave by the a wave reduces the influence of the factors other than fatigue, thereby improving the accuracy of the fatigue assessment compared to the case in which the fatigue is assessed based on the peak value of the accelerated plethysmogram itself.

In addition, it is preferable that the human fatigue assessment device further includes a device controller for controlling an external device which stimulates the user when the fatigue determining unit determines that the user is fatigued.

Furthermore, the configuration allows displaying the result of fatigue assessment and automatically providing a care based on the assessment result by stimulating the user when it is determined that the user is fatigued.

In addition, it is preferable that the physiological signal measuring unit is further measures a heartbeat or pulse wave of the user as a physiological signal, the feature value extracting unit further extracts second feature values each indicating amount of parasympathetic nerve activity, and each obtained from the physiological signal measured by the physiological signal measuring unit, the storage unit further stores the second feature values extracted by the feature value extracting unit, the human fatigue assessment device further includes a fatigue type determining unit which determines a type of the fatigue of the user as to whether the fatigue is due to difficult work or due to monotonous work, and when the fatigue determining unit determines that the user is fatigued, the fatigue type determining unit determines the type of fatigue by comparing a second feature value among the second feature values extracted by the feature value extracting unit and at least one of the second feature values stored in the second feature values stored in the storage unit.

This configuration allows a determination on the type of the fatigue when the user is fatigued as to whether the fatigue is due to difficult work or monotonous work, by using the second feature values, making it possible to support the user in a suitable way. Furthermore, the determination is made by using the physiological signal which includes the heartbeat and pulse wave, which can be easily measured regardless of the situation.

In addition, it is preferable that the fatigue type determining unit determines that the fatigue is due to difficult work when the second feature values decrease in time-series, and determines that the fatigue due to monotonous work when the second feature values do not decrease in time-series.

This configuration allows determining the type of fatigue based on the change of the second feature values in time-series, making it possible to support the user for recovery in a suitable manner. Furthermore, this configuration is highly versatile since the type of fatigue can be determined based on the physiological signal which can be easily measured regardless of the situation.

In addition, it is preferable that the physiological signal measuring unit further measures a brain signal of the user as a physiological signal, the feature value extracting unit further extracts third feature values each of which is obtained from the physiological signal measured by the physiological signal measuring unit, and is related to at least one of a β wave and an α wave, the storage unit stores the third feature values extracted by the feature value extracting unit, the human fatigue assessment device further includes a fatigue type determining unit which determines a type of the fatigue of the user as to whether the fatigue is due to difficult work or due to monotonous work, using the third feature values extracted by the feature value extracting unit, and when the fatigue determining unit determines that the user is fatigued, the fatigue type determining unit determines the type of fatigue by comparing a third feature value among the third feature values extracted by the feature value extracting unit and at least one of the third feature values stored in the storage unit.

This configuration allows a determination on the type of the fatigue when the user is fatigued as to whether the fatigue is due to difficult work or monotonous work, by using the third feature values, making it possible to support the user in a suitable way. In addition, the type of fatigue can be determined based on the brain signal. Thus, it is widely applicable for managing people with an occupation wearing hats or headsets at work.

In addition, it is preferable that the human fatigue assessment device further includes a checking unit which generates checking information for checking whether the user is in an open-eye state or in a closed-eye state, in which the physiological signal measuring unit attaches the checking information to the measured physiological signal, and the feature value extracting unit extracts the third feature values each of which is using at least one of a power value in a $\beta$ waveband and a power value in an $\alpha$ waveband that are in a time period in which the checking unit determines that the user is in the open-eye state or the closed-eye state.

With this configuration, at least one of the power value in the $\beta$ waveband and the power value in the $\alpha$ waveband in the grain signal is used for $\alpha$ value when the user is in the open-eye state or $\alpha$ value when the user is in the closed-eye state. Thus, it is possible to further improve the accuracy of the fatigue assessment.

In addition, it is preferable that the feature value extracting unit extracts the third feature values each of which is using the power value in the $\alpha$ waveband in the time period in which the checking unit determines that the user is in the closed-eye state, and the fatigue type determining unit determines that the fatigue is due to difficult work when the third feature values increase in time-series.

With this configuration, whether the fatigue of the user is due to difficult work is determined based on the power value in the $\alpha$ waveband in the time period when the user is in the closed-eye state. Thus, it is possible to further improve the accuracy of the fatigue assessment. Furthermore, it is possible to support the user for recovery in a suitable manner from the fatigue due to difficult work determined by the determining on the type of fatigue.

In addition, it is preferable that the feature value extracting unit extracts the third feature values each of which is using the power value in the $\beta$ waveband in the time period in which the checking unit determines that the user is in the open-eye state or the closed-eye state, and the fatigue type determining unit determines that the fatigue is due to monotonous work when the third feature values decrease in time-series.

With this configuration, whether or not the fatigue of the user is due to monotonous work is determined based on the power value in the $\beta$ waveband in the time period in which the user is determined to be in the open-eye state or in the closed-eye state, thereby improving the accuracy of the fatigue assessment. Furthermore, it is possible to support the user for recovery in a suitable manner from the fatigue due to difficult work determined by the determining on the type of fatigue.

In addition, it is preferable that the human fatigue assessment device further includes: a stimulation output unit which outputs audio stimulation for stimulating the user's auditory sense; and a fatigue type determining unit which determines a type of the fatigue of the user as to whether the fatigue is due to difficult work or due to monotonous work, using the first feature values extracted by the feature value extracting unit, in which, when the fatigue determining unit determines that the user is fatigued, the fatigue type determining unit is configured to determine the type of the fatigue by comparing (i) first feature values stored in the storage unit in a time period before an output of audio stimulation by the stimulation output unit and (ii) first feature values in a time period when the stimulation output unit outputs the audio stimulation.

With this configuration, the type of the fatigue as to whether the fatigue of the user is due to difficult work or monotonous work can be determined by outputting the audio stimulation. Thus, it is possible to support the user for recovery in a suitable manner. Furthermore, the type of fatigue is determined using the pulse wave which can be easily measured regardless of the scene and the audio stimulation which does not require a specific device. Thus, this configuration is widely applicable to uses including measuring the driver's pulse wave from a part in contact with the driver when he/she is driving, and determining the type of the fatigue using the pulse wave signal in response to the sound stimulation output from a car navigation system, for example.

In addition, it is preferable that the feature value extracting unit calculates an accelerated plethysmogram from the pulse wave signal, and to extract a ratio of a peak value of the c wave with respect to a peak value of the a wave in the plethysmogram as the first feature value, and the fatigue type determining unit determines that the fatigue is due to monotonous work when the first feature values in the time period in which the stimulation output unit outputs the audio stimulation are increased from the first feature values stored in the storage unit in a time period before the output of the audio stimulation by the stimulation output unit, and to determine that the fatigue is due to difficult work when the first feature values in the time period in which the stimulation output unit outputs the audio stimulation are not increased from the first feature values stored in the storage unit in a time period before the output of the audio stimulation by the stimulation output unit.

With this configuration, it is possible to determine the type of fatigue of the user as to whether the fatigue is due to difficult work or due to monotonous work, allowing to support the user for recovery in a suitable manner. Furthermore, it is possible to determine the type of fatigue using the pulse wave which can be easily measured regardless of the scene and the audio stimulation which does not require a specific device, thereby making this configuration widely applicable.

In addition, it is preferable that the human fatigue assessment device further includes a device controller for controlling an external device which stimulates the user according to the type of fatigue determined by the fatigue type determining unit.

In addition, this configuration allows presentation of the determination result of the type of fatigue to the user and to suitably assist the user's recovery by stimulating the user according to the type of fatigue.

In order to solve the problems, the human fatigue assessment device according to an aspect of the present invention includes a physiological signal measuring unit which measures a heartbeat or pulse wave of a user as a physiological signal; a feature value extracting unit which extracts second feature values each indicating amount of parasympathetic nerve activity and each obtained from the physiological signal measured by the physiological signal measuring unit; a storage unit in which the second feature values extracted by the feature value extracting unit; and a fatigue type determining unit which determines a type of the user's fatigue as to whether the fatigue is due to difficult work or due to monotonous work, using the second feature values extracted by the feature value extracting unit, in which the fatigue type determining unit determines the type of the user's fatigue by comparing a second feature value among the second feature values extracted by the feature value extracting unit and at least one of the second feature values stored in the storage unit.

With this configuration, it is possible to determine the type of fatigue of the user as to whether the fatigue is due to difficult work or due to monotonous work by using the second feature values, allowing to support the user for recovery in a suitable manner. Furthermore, the determination is made by using the physiological signal which includes the heartbeat and pulse wave, which can be easily measured regardless of the situation.

In order to solve the problems, the human fatigue assessment device according to an aspect of the present invention includes a physiological signal measuring unit which measures a brain signal of a user as a physiological signal; a feature value extracting unit which extracts third feature values each of which is obtained from the physiological signal measured by the physiological signal measuring unit and related to at least one of a β wave and an α wave; a storage unit in which the third feature values extracted by the feature value extracting unit is stored; and a fatigue type determining unit which determines a type of the user's fatigue as to whether the fatigue is due to difficult work or due to monotonous work, using the third feature values extracted by the feature value extracting unit, in which the fatigue type determining unit determines the type of the fatigue by comparing a third feature value among the third feature values extracted by the feature value extracting unit and at least one of the third feature values stored in the storage unit.

With this configuration, it is possible to determine the type of fatigue of the user as to whether the fatigue is due to difficult work or due to monotonous work by using the third feature values, allowing to support the user for recovery in a suitable manner. In addition, the type of fatigue can be determined based on the brain signal. Thus, it is widely applicable for managing people with an occupation wearing hats or headsets at work.

In order to solve the problems, the human fatigue assessment device according to an aspect of the present invention includes a stimulation output unit which outputs audio stimulation for stimulating a user's auditory sense; a physiological signal measuring unit which measures a pulse wave signal of the user; a feature value extracting unit which extracts first feature values each of which is obtained from a systolic posterior component of the pulse wave signal measured by the physiological signal measuring unit; a storage unit in which the first feature values extracted by the feature value extracting unit is stored; and a fatigue type determining unit which determines a type of the fatigue of the user whether it is fatigue due to difficult work or due to monotonous work, using the first feature values extracted by the feature value extracting unit, in which the fatigue type determining unit determines the type of the fatigue by comparing (i) first feature values stored in the storage unit in a time period before an output of audio stimulation by the stimulation output unit and (ii) first feature values in a time period when the stimulation output unit outputs the audio stimulation.

With this configuration, the type of the fatigue as to whether the fatigue of the user is due to difficult work or monotonous work can be determined by outputting the audio stimulation. Thus, it is possible to support the user for recovery in a suitable manner. Furthermore, the type of fatigue is determined using the pulse wave which can be easily measured regardless of the scene and the audio stimulation which does not require a specific device. Thus, it is widely applicable and possible to measure the driver's pulse wave through a part in contact with the driver when he/she is driving, and to determine the type of the fatigue using the pulse wave signal in response to the sound stimulation output from a car navigation system, for example.

Furthermore, not only the present invention can be implemented as a human fatigue assessment device, but also as a human fatigue assessment method which includes processes performed by the processing units in the human fatigue assessment device as steps. In addition, the present invention can be implemented as a program causing a computer to execute unique processes in the human fatigue assessment method. Needless to say, the program can be distributed via recoding media such as CD-ROM and transmission media such as the Internet. Alternatively, the present invention may be implemented as an integrated circuit including characteristic units included in the human fatigue assessment device.

Advantageous Effects of Invention

According to the present invention, it is possible to perform highly precise fatigue assessment.

BRIEF DESCRIPTION OF DRAWINGS

FIG. 3A is a flowchart illustrating an example of fatigue assessment by a fatigue determining unit according to Embodiment 1.

FIG. 3B is a flowchart illustrating another example of fatigue assessment by the fatigue determining unit according to Embodiment 1.

FIG. 6 is a block diagram illustrating a configuration of a human fatigue assessment device according to Embodiment 3.

FIG. 7A is a flowchart illustrating an example of determining a type of fatigue by a fatigue type determining unit using a power value in α band frequency according to Embodiment 3.

FIG. 7B is a flowchart illustrating an example of determining a type of fatigue by the fatigue type determining unit using α-blocking according to Embodiment 3.

FIG. 8A is a flowchart illustrating an example of determining a type of fatigue by a fatigue type determining unit using a power value in α band frequency according to Embodiment 3.

FIG. 8B is a flowchart illustrating an example of determining a type of fatigue by the fatigue type determining unit using a power value in α band frequency and a mean frequency according to Embodiment 3.

FIG. 15A illustrates subjective report scores before and after the mental fatigue stress.

FIG. 15B illustrates subjective report scores at the time of N-back test recorded after the end of the test.

FIG. 16B illustrates a change in the peak value of APG waveforms before and after the mental fatigue stress (2-back).

FIG. 25A is a block diagram illustrating a configuration of a conventional human fatigue assessment device.

FIG. 25B is a block diagram illustrating a configuration of a conventional human fatigue assessment device.

DESCRIPTION OF EMBODIMENTS

Figure 1:
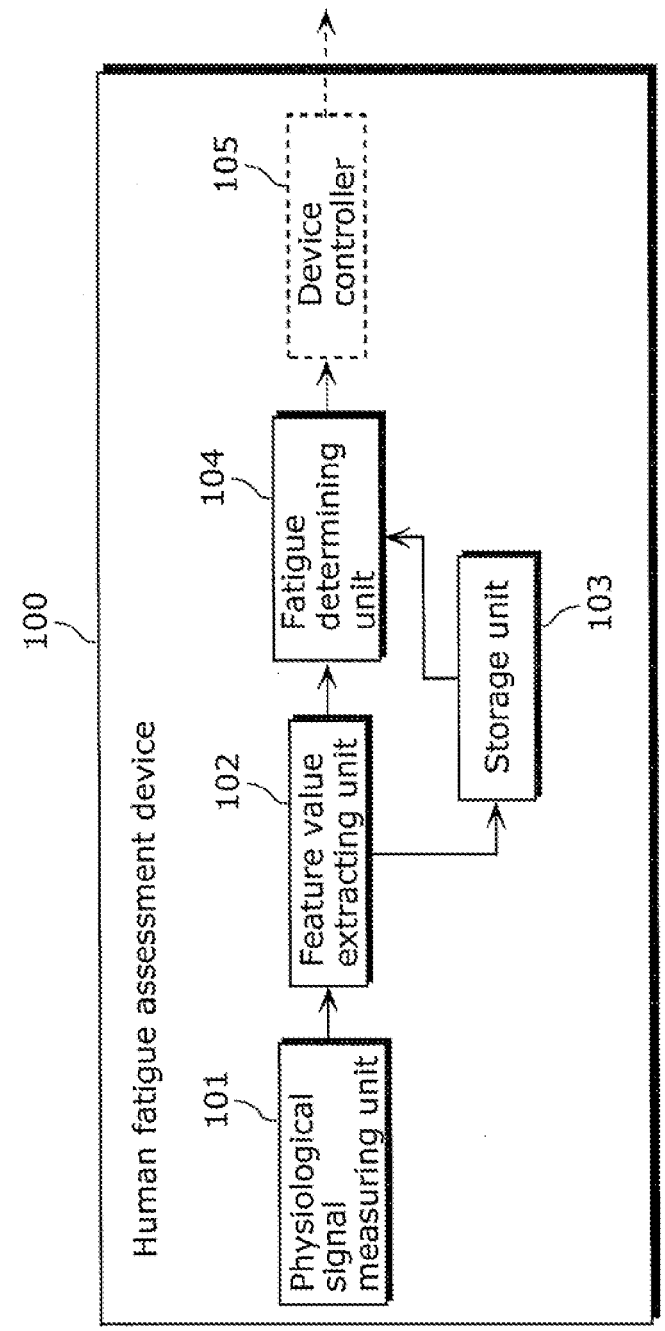
FIG. 1 is a block diagram illustrating a configuration of a human fatigue assessment device according to Embodiment 1.

The following shall describe embodiments of the present invention with reference to the drawings. Note that, the same reference numerals are assigned to the same components, and the description for the components may be omitted.

Embodiment 1

FIG. 1 is a block diagram illustrating a configuration of the human fatigue assessment device 100 according to Embodiment 1 of the present invention.

As illustrated in FIG. 1, the human fatigue assessment device 100 includes a physiological signal measuring unit 101 which measures pulse signals of a user, a feature value extracting unit 102 which extract a feature value from the pulse signals, a storage unit 103 which stores the feature value, and a fatigue determining unit 104 which determines whether or not the user is fatigued. Note that, as illustrated in FIG. 1, the human fatigue assessment device 100 may further include a device controller 105 which controls external devices based on the result of fatigue assessment.

The physiological signal measuring unit 101 samples the user's pulse waves detected by transducers and others in a predetermined sampling cycle, and obtains pulse wave data in time-series. Fingertips or earlobes are typical parts for attaching the physiological signal measuring unit 101. However, the biological signal measuring unit 101 may be attached to any part of the body that allows taking pulse waves, including forehead or a tip of nose, for example.

The feature value extracting unit 102 extracts a first feature value obtained from the systolic posterior component of the pulse wave signal measured by the physiological signal measuring unit 101. More specifically, the feature value extracting unit 102 calculates accelerated plethysmogram from the pulse wave signal, and extracts the first feature value using information on component waves including at least information on c wave and d wave, which are in component waves of the accelerated plethysmogram corresponding to the systolic posterior component.

The storage unit 103 is a memory for storing the first feature value extracted by the feature value extracting unit 102.

The fatigue determining unit 104 determines whether or not the user is fatigued, using the first feature value extracted by the feature value extracting unit 102. More specifically, the fatigue determining unit 104 determines whether or not the user is fatigued by comparing one of the first feature values extracted by the feature value extracting unit 102 and at least one of the first feature values stored in the storage unit 103. For example, the fatigue determining unit 104 determines whether or not the user is fatigued by comparing the currently extracted first feature value and the first feature value extracted in the past, among the extracted first feature values.

For example, when a ratio of a peak value of the c wave with respect to the a wave, the b wave, or the e wave in the accelerated plethysmogram is extracted as the first feature value, the fatigue determining unit 104 determines that the user is fatigued when an absolute values of the first feature value increases in time series.

Alternatively, when the feature value extracting unit 102 extracts the difference between peak values of the a wave and the c wave in the accelerated plethysmogram as the first feature value, the fatigue determining unit 104 determines that the user is fatigued when the absolute values of the first feature values decrease in time series.

Furthermore, when the feature value extracting unit 102 extracts a value calculated by dividing the difference between the peak value of the c wave and the peak value of the d wave in the accelerated plethysmogram by the a wave in the accelerated plethysmogram as the first feature value, the fatigue determining unit 104 determines that the user is fatigued when the absolute values of the first feature value increase in time series.

Figure 2B:
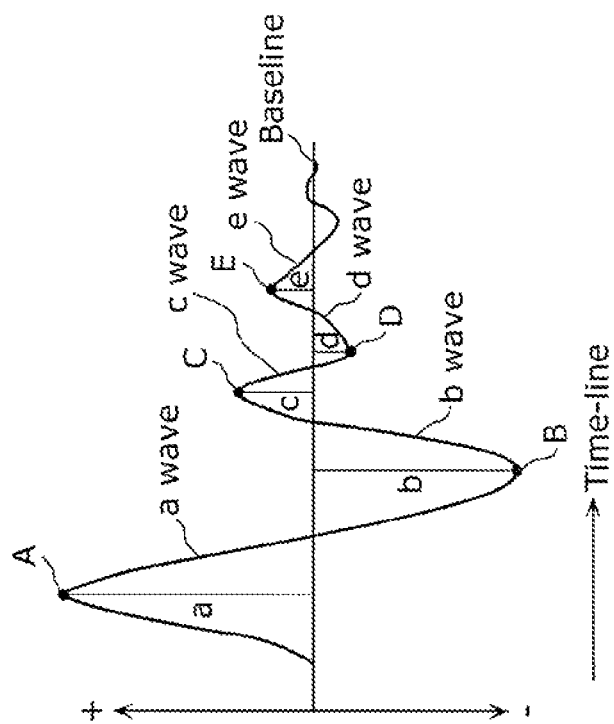
FIG. 2B illustrates an example of accelerated plethysmogram waveform.
Figure 2A:
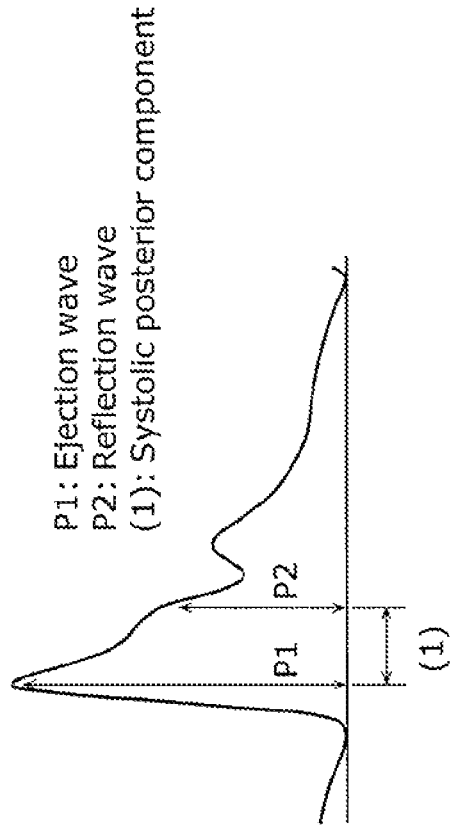
FIG. 2A illustrates an example of photoplethysmogram.

FIG. 2A illustrates an example of plethysmogram (abbreviated as PTG) waveform measured by the physiological signal measuring unit 101. FIG. 2B illustrates an example of accelerated plethysmogram (abbreviated as APG) waveform which is a second order differential of the plethysmogram in FIG. 2A.

As illustrated in FIG. 2A, an ejection wave (P1) and a reflection wave (P2) are detected in a plethysmogram. As illustrated in FIG. 2B, the waveform of the accelerated plethysmogram includes an early systolic positive wave (a wave), an early systolic negative wave (b wave), a mid-systolic re-elevating wave (c wave), an end systolic re-depressing wave (d wave), and an early diastolic positive wave (e wave).

In terms of a correspondence between the plethysmogram illustrated in FIG. 2A and accelerated plethysmogram in FIG. 2B, the a wave and the b wave of the accelerated plethysmogram waveform component are included in the systolic anterior component of the plethysmogram, and the c wave and the d wave of the accelerated plethysmogram waveform component are included in the systolic posterior component. The systolic anterior component of the plethysmogram reflects driving pressure wave caused by ejected blood, and the systolic posterior component of the plethysmogram reflects a reflecting pressure wave which is the driving pressure wave propagated to periphery and returning back.

Inventors of the present invention found out that, among the accelerated plethysmogram waveform component which is a second order differential of the pulse wave, the peak value of the a wave, the peak value of the b wave, and the peak value of the e wave significantly change before and after mental fatigue stress through a potentiality demonstration experiment regarding non-invasive assessment of the human fatigue. Here, the significant change refers to a change satisfying a statistical significance level of 5% or 1%.

On the other hand, the inventors also found out that the peak value of the c wave and the peak value of the d wave which are feature values reflecting the systolic posterior component of the pulse wave do not significantly change before and after the mental fatigue stress (in other words, not change accompanying with the fatigue was found). Furthermore, the inventors found out that the feature value using accelerated plethysmogram waveform components including the c wave and the d wave significantly changes before and after the mental fatigue stress. In the following description, the peak values of the a wave to the e wave are referred to as "a" to "e".

A c/a value which is a peak ratio of the c wave and the a wave, a c/b value which is a peak ratio of the c wave and the b wave, and a c/e value which is a peak ratio of the c wave and the e wave are feature values using the information of the accelerated plethysmogram waveform components including the c wave and the d wave. Furthermore, an a−c value or a c−a value which are peak differences between the c wave and the a wave, and |d−c|/a value obtained by dividing the peak difference between the c wave and the d wave by the peak value of the a wave. The potentiality demonstration experiment regarding non-invasive assessment of human fatigue performed by the inventors shall be described later in detail.

Here, the description shall be made using an example in which the feature value extracting unit 102 extracts the c/a value, among other feature value.

First, the feature value extracting unit 102 converts the pulse wave signals measured by the physiological signal measuring unit 101 to an accelerated plethysmogram waveform illustrating in FIG. 2B by obtaining a second order differential of the pulse signal.

Furthermore, the feature value extracting unit 102 extracts a peak value "a" of the a wave from an earliest extreme value in time among the accelerated plethysmogram waveform components, is extracts, a peak value "c" of then wave from the third extreme value in time, and calculates the c/a value, which is a ratio between them. The feature value extracting unit 102 stores the calculated c/a values in the storage unit 103 in time series.

Note that, the feature value extracting unit 102 may output, as the c/a value, a value for one beat of pulse wave signal without any modification, or output an average value within a predetermined time period (for example, 10 seconds).

The fatigue determining unit 104 compares c/a values in at least two points in time, and determines whether or not the user is fatigued. For example, when a new c/a value is output from the feature value extracting unit 102, the fatigue determining unit 104 compares a current c/a value and a c/a value at one point before in time series among the c/a values stored in the storage unit 103.

Of course, it is not limited to this example, and the fatigue determining unit 104 may compare the current c/a value and a c/a value stored in a predetermined timing (for example, immediately after the activation) as a reference value. Note that, as other comparison methods, the fatigue determining unit 104 may compare a sum of all c/a values at all points in time between the present time and a predetermined period in the past. Furthermore, the fatigue determining unit 104 may determine that the user is fatigued when the sum of the c/a values is a predetermined threshold or more.

FIGS. 3A and 3B are flowcharts illustrating an example of fatigue assessment by the fatigue determining unit 104 according to Embodiment 1.

First, operation of the fatigue determining unit 104 illustrated in FIG. 3A shall be described. When the feature value extracting unit 102 outputs the c/a value (step S31), the fatigue determining unit 104 calls a c/a value at one point before in time series among the c/a values stored in the storage unit 103 (step S32).

Subsequently, the fatigue determining unit 104 compares the two c/a values, that is, the current c/a value and the c/a value at one point before in time (step S33).

When the fatigue determining unit 104 determines that the current c/a value is larger than the c/a value at one point before in time (Yes in step S33), the fatigue determining unit 104 determines that the user is fatigued (step S34).

Furthermore, when the fatigue determining unit 104 determines that the current c/a value is no larger than the c/a value at one point before in time (No in step S33), the fatigue determining unit 104 waits until the feature value extracting unit 102 outputs a c/a value, and repeats the operation from step S31 after the output of the next c/a value.

The fatigue determining unit 104 may also perform operations illustrated in FIG. 3B. When performing the operations illustrated in FIG. 3B, the operation flow from step S31 to step S33 is the same as the example illustrated in FIG. 3A.

When the fatigue determining unit 104 determines that the current c/a value is larger than the c/a value at one point before in time in step S33 (Yes in step S33), the fatigue determining unit 104 calculates the amount of change from the c/a value at one point before in time to the current c/a value, and compares the calculated amount of the change with a preset threshold L1 (for example, the amount of change of approximately 0.03 (step S35).

When the fatigue determining unit 104 determines that the calculated amount of change is larger than the threshold L1 (Yes in step S35), the fatigue determining unit 104 determines that the user is fatigued (step S36).

When the fatigue determining unit 104 determines that the current c/a value is not larger than the c/a value at one point before in time, or when it is determined that the calculated amount of change is not larger than the threshold L1 (No in step S35), the fatigue determining unit 104 waits until a next c/a value is output from the feature value extracting unit 102, and repeats the operations from step S31 after the output of the next c/a value is output.

Note that, the threshold L1 is not limited to a value approximately 0.03. However, in view of the result of the experiment to be described later, it is preferable to set the threshold L1 to a value from approximately 0.03 to approximately 0.035 (see FIG. 17).

The fatigue determining unit 104 determines whether or not the user is fatigued by outputting information including 1 in the case of fatigued and outputting the information including 0 in the case of not fatigued.

When the human fatigue assessment device 100 includes the device controller 105, the device controller 105 controls external devices based on the result of the determination by the fatigue determining unit 104. For example, the device controller 105 may output the result of fatigue determining to a user or a section managing and supervising the user by controlling a display with a display function or controlling the speaker which outputs sound.

Furthermore, when the fatigue determining unit 104 determines that the user is fatigued, the device controller 105 may control external devices which stimulate the user. For example, the device controller 105 may control a device which generates a scent or heat to generate a scent, an air current, or a heat effective for recovering from or reducing fatigue. Alternatively, the device controller 105 may store, accumulate, and transmit the results determined by the fatigue determining unit 104.

As described above, the human fatigue assessment device 100 determines whether or not the user is fatigued based on the feature value extracted from the accelerated plethysmogram waveform components including the c wave and the d wave which changes specifically to fatigue among the pulse wave signals.

With the configuration described above, whether or not the user is fatigued is determined by extracting the first feature value obtained from the systolic posterior component of the pulse wave signal, and comparing a first feature value of the extracted first feature values and at least one of the first feature values stored in the storage unit 103. Here, although the systolic posterior component of the pulse wave signal is affected by factors other than fatigue, it is not susceptible to the influence of fatigue. Thus, by using the first feature value obtained from the systolic posterior component reduces the influence of factors other than the fatigue included in the pulse wave, improving the accuracy of the fatigue assessment.

Furthermore, this configuration using the information of the c wave or the d wave reduces the influence of the factors other than fatigue compared to a case in which the fatigue is assessed based on the peak value of the accelerated plethysmogram waveform itself, and improves the accuracy of the fatigue assessment.

In addition, with this configuration using the ratio of the c wave with respect to the peak values of the a wave, the b wave, or the e wave improves the accuracy of the fatigue assessment by reducing the influence of the factors other than fatigue compared to a case in which the fatigue is assessed based on the peak value of the accelerated plethysmogram waveform itself.

Furthermore, this configuration using the difference between the peak value of the a wave and the peak value of the c wave reduces the influence of the factors other than fatigue compared to a case in which the fatigue is assessed based on the peak value of the accelerated plethysmogram waveform itself, and improves the accuracy of the fatigue assessment.

Furthermore, this configuration using a value obtained by dividing the difference between the peak value of the c wave and the peak value of the d wave by the a wave reduces the influence of the factors other than fatigue, thereby improving the accuracy of the fatigue assessment, compared to a case in which the fatigue is assessed based on the peak value of the accelerated plethysmogram itself.

Furthermore, the configuration allows displaying the result of fatigue assessment and automatically providing a care based on the assessment result by stimulating the user when it is determined that the user is fatigued.

Note that, when the human fatigue assessment device 100 does not include the device controller 105, the external devices may be controlled by an external structure.

Embodiment 2

Figure 4:
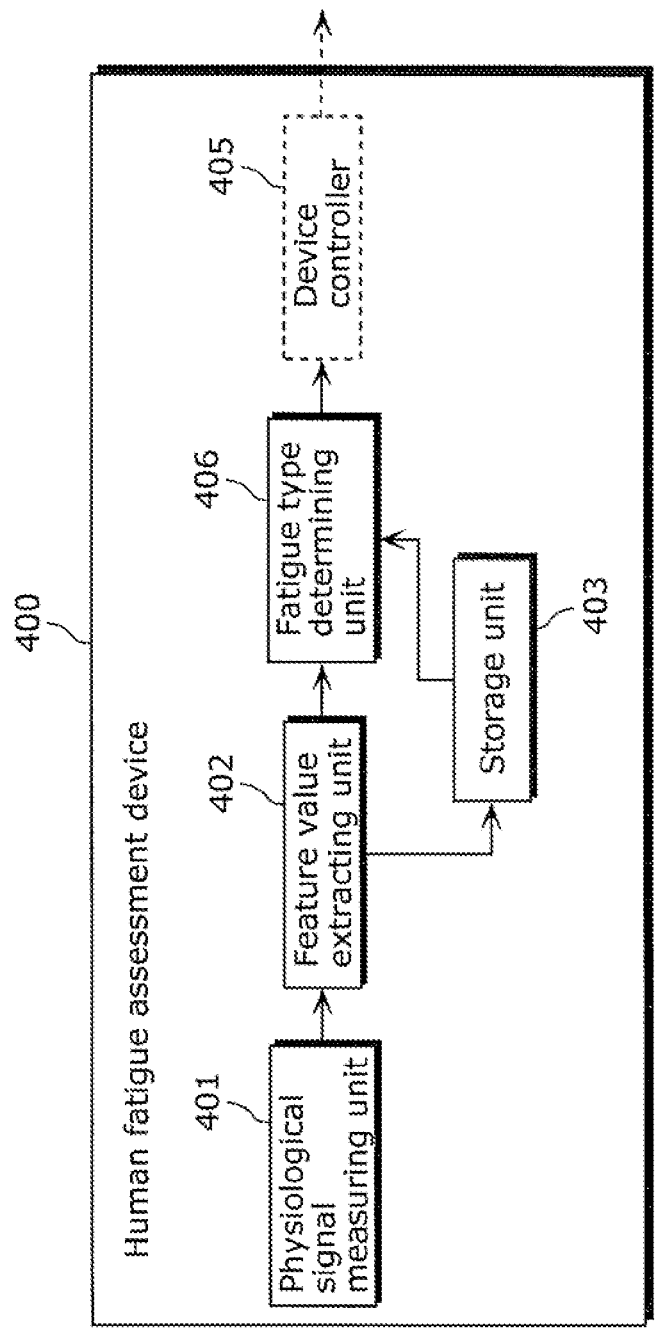
FIG. 4 is a block diagram illustrating a configuration of a human fatigue assessment device according to Embodiment 2.

FIG. 4 is a block diagram illustrating a configuration of the human fatigue assessment device 400 according to Embodiment 2 of the present invention.

As illustrated in FIG. 4, the human fatigue assessment device 400 includes a physiological signal measuring unit 401 which measures physiological signals, a feature value extracting unit which extracts feature value from the physiological signals, a storage unit 403 which stores the feature value, and a fatigue type determining unit 406 which determines a type of fatigue. Note that, as illustrated in FIG. 4, the human fatigue assessment device 400 may further include a device controller 405 which controls external devices based on the result of fatigue assessment.

The physiological signal measuring unit 401 measures heartbeat or the pulse waves of the user as the physiological signals. More specifically, the physiological signal measuring unit 401 is a living body sensor which measures physiological signals such as electrocardiograms, pulse waves, brain waves, and magnetoencephalography.

Electric charge in living body such as electrocardiograms and brain waves are typically derived outside of the body as electric signals through multiple electrodes attached on the surface of the skin of living body. Magnetic quantity in living body such as magnetoencephalography is measured by a flux-gate magnetometer or a superconductive quantum interferometer of higher sensitivity for measuring a weak magnetic flux density. Pulse waves are typically obtained by irradiating the living body with infrared light using a light source such as an LED, and by converting the light intensity transmitted the living body into electric signals by a photodiode to obtain the electric signals.

Through the potentiality demonstration experiment, the inventors found out that the types of fatigue and the amount of parasympathetic nerve activity, which is one of the autonomous nerve activity are related. The types of fatigue include the fatigue caused by difficult work (hereafter referred to as fatigue due to difficult work) and the fatigue caused by monotonous work (hereafter referred to as fatigue due to monotonous work). More specifically, the inventors found out the tendency that the amount of parasympathetic nerves significantly decreases at the time of fatigue due to difficult work, while the amount of parasympathetic nerve activity does not decrease at the time of fatigue due to monotonous work. In other words, no decrease is found in the amount of parasympathetic nerve activity accompanying the fatigue due to monotonous work.

Index values indicating the amount of parasympathetic nerve activity includes a power value in high frequency (hereafter referred to as HF) band between 0.15 Hz and 0.4 Hz in the power spectrum calculated by performing frequency analysis on time-series data of intervals of the a wave between heartbeats in electrocardiogram and between pulses. The index value indicating the amount of parasympathetic nerve activity is not limited to the power values, and it may be ln HF, which is a logarithm of the HF power value. Alternatively, % HF which is obtained by dividing the HF power value by a total power value which includes other bands in the power spectrum such as very low frequency (VLF) which is 0.04 Hz or less, and low frequency (LF) which is between 0.04 Hz and 0.15 Hz may also be used. The potentiality demonstration experiment regarding the non-invasive assessment of human fatigue performed by the inventors shall be described later in detail.

Here, the operations of the human fatigue assessment device 400 shall be described as follow using an example in which the index value of the amount of parasympathetic nerve activity is a value calculated using pulse waves.

First, the physiological signal measuring unit 401 measures the pulse waves of the user as the physiological signals.

The feature value extracting unit 402 extracts a second feature value indicating the amount of parasympathetic nerve activity obtained from the physiological signal measured by the physiological signal measuring unit 401.

More specifically, the feature value extracting unit 402 calculates the amount of parasympathetic nerve activity which is one of autonomous nerve activity by calculating an interval between the a waves (hereafter referred to as a-a interval) between pulses from the accelerated plethysmogram waveform which is a second order differential of the pulse signals measured by the physiological signal measuring unit 401, and using the time-series data of the a-a interval. For example, the feature value extracting unit 402 performs a frequency analysis on the time series data of the a-a interval using the fast Fourier transform (FFT) and the maximum entropy method (MEM) to calculate the HF power value in the power spectrum.

Subsequently, the feature value extracting unit 402 stores the calculated HF power values in the storage unit 403 in time-series. Note that, the feature value extracting unit 402 may use, as the HF power value, the calculated value in a minimum time period necessary for performing the frequency analysis (for example, for 30 seconds) or a mean value in a predetermined period obtained by collecting the calculated values in the minimum time periods in time-series (for two minutes, for example).

The storage unit 403 is a memory for storing the second feature value extracted by the feature value extracting unit 402. More specifically, the storage unit 403 accumulates the HF power values in time-series each time the HF power value is output from the feature value extracting unit 402 as the feature value.

The fatigue type determining unit 406 determines the type of fatigue of the user whether it is the fatigue due to difficult work or the fatigue due to monotonous work, using the second feature value extracted by the feature value extracting unit 402.

More specifically, the fatigue type determining unit 406 compares the HF power values at least in two points in time to determine the type of fatigue. More specifically, the fatigue type determining unit 406 determines the type of fatigue by comparing a feature value among the second feature values extracted by the feature value extracting unit 402 and at least one of the second feature values stored in the storage unit 403.

For example, when the feature value extracting unit 402 outputs a new HF power value, the fatigue type determining unit 406 compares the current HF power value and the power value at one point before in time among the HF power values in time-series stored in the storage unit 403. Certainly, the determining of the type of fatigue by the fatigue type determining unit 406 is not limited to this example. For example, the comparison with the current HF power value may be performed using the HF power value stored with a predetermined timing (for example, immediately after activation) as a reference value.

Subsequently, when the second feature values decrease in time-series, the fatigue type determining unit 406 determines that the fatigue is due to difficult work, and when the second feature values do not decrease in time-series, the fatigue type determining unit 406 determines that the fatigue is due to monotonous work.

Figure 5A:
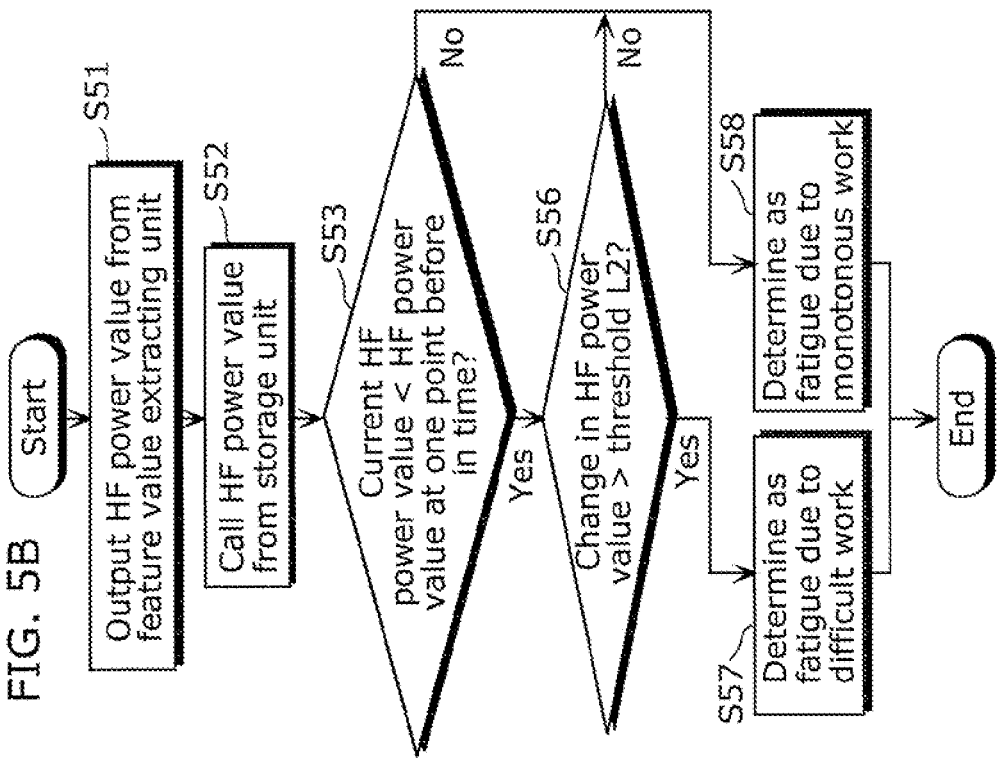
FIG. 5A is a flowchart illustrating an example of determining a type of fatigue by a fatigue type determining unit according to Embodiment 2.
Figure 5B:
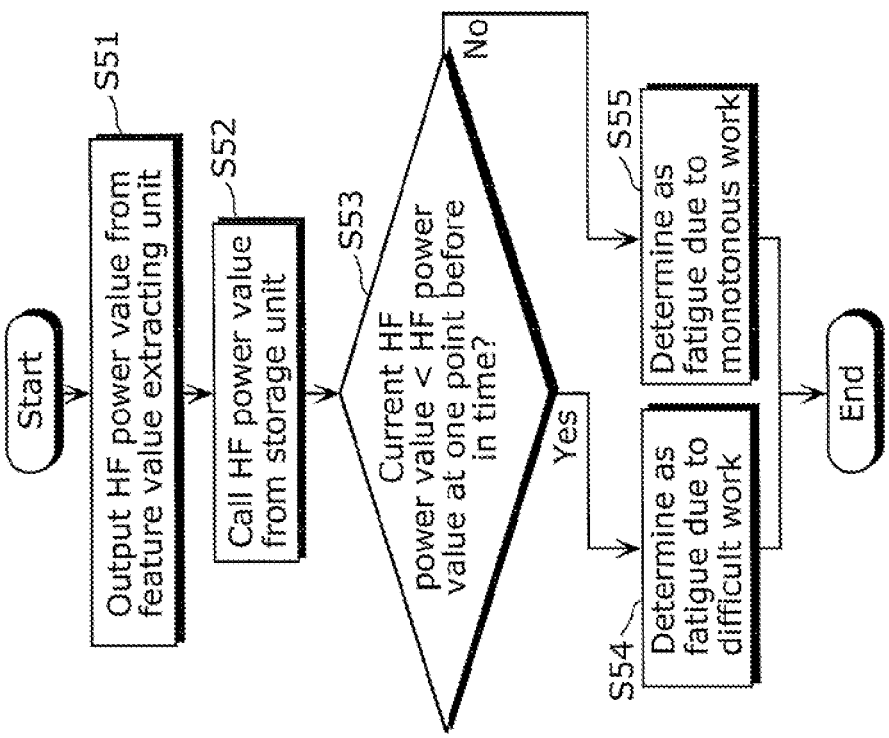
FIG. 5B is a flowchart illustrating another example of determining a type of fatigue by the fatigue type determining unit according to Embodiment 2.

FIGS. 5A and 5B are flowcharts illustrating an example of determining type of fatigue by the fatigue type determining unit 406 according to Embodiment 2.

First, operation of the fatigue determining unit 406 illustrated in FIG. 5A shall be described. When the feature value extracting unit 402 outputs the HF power value (step S51), the fatigue type determining unit 406 calls the HF power value at one point before in time among the HF power values stored in the storage unit 403 in time-series (step S52).

Subsequently, the fatigue type determining unit 406 compares the two HF power value, namely, the current HF power value and the HF power value at one point before in time (step S53).

When the fatigue type determining unit 406 determines that the current HF power value is smaller than the HF power value at one point before in time (Yes in step S53), it determines that the fatigue is due to difficult work (step S54).

Alternatively, when the fatigue type determining unit 406 determines that the current HF power value is no smaller than the HF power value at one point before in time (No in step S53), it is determined that the fatigue is due to monotonous work (step S55).

Subsequently, the fatigue type determining unit 406 repeats the operations from step S51, after the feature value extracting unit 402 outputs the HF power value.

Note that, other comparison methods by the fatigue type determining unit 406 at two or more points in time includes a comparison between the sum of all of the HF power values between the current point in time and a point for a predetermined period before and a predetermined threshold. Subsequently, when the sum of the HF power value is a predetermined threshold or less, the fatigue type determining unit 406 may determine that the fatigue is due to difficult work, and when the sum of the HF power value is more than a predetermined threshold, the fatigue type determining unit 406 may determine that the fatigue is due to monotonous work.

The fatigue type determining unit 406 may also perform the operations illustrated in FIG. 5B. When performing the operations illustrated in FIG. 5B, the operation flow from step S51 to step S53 is the same as the example, illustrated in FIG. 5A.

When the fatigue type determining unit 406 determines that the current HF power value is smaller than the HF power value at one point before in time in step S53 (Yes in step S53), the fatigue type determining unit 406 calculates the amount of change from the HF power value at one point before in time to the current HF power value, and compares the amount of change and a predetermined threshold L2 (for example, the amount of change in the HF power value which makes the amount of change in ln HF to be approximately 0.3) (step S56).

When the fatigue type determining unit 406 determines that the calculated amount of change is larger than the threshold L2 (Yes in step S56), the fatigue type determining unit 406 determines that the fatigue is due to difficult work (step S57).

Alternatively, when the fatigue type determining unit 406 determines that the current HF power value is not smaller than the HF power value at one point before in time (No in step S53) or when the fatigue type determining unit 406 determines that the calculated amount of change is no larger than the threshold L2 (No in step S56), it determines that the fatigue is due to monotonous work (step S58).

Subsequently, the fatigue type determining unit 406 repeats the operations after step S51 when the feature value extracting unit 402 outputs the HF power value.

Note that, the threshold L2 is not limited to the amount of change in HF power values which makes the amount of change in ln HF to be approximately 0.3. However, in view of the experiment results to be described alter, it is preferable to set the amount of change in the HF power value to a value which makes the amount of change in ln HF to be approximately between 0.25 and 0.4 (see FIG. 20).

When the human fatigue assessment device 400 includes the device controller 405, the device controller 405 controls the external devices based on the result determined by the fatigue type determining unit 406. For example, the device controller 405 may control devices such as a display with display function or a speaker which outputs sound to notify the user or the section managing and supervising the user of the results of determining the type of fatigue.

Alternatively, the device controller 405 may control external devices for stimulating the user according to the type of fatigue determined by the fatigue type determining unit 406. For example, the device controller 405 may control a device which generates air current or heat to output stimulation such as a scent, an air current, or a heat suitable for a recovery from fatigue or reducing fatigue. Alternatively, the device controller 405 may store and accumulate the result determined by the fatigue type determining unit 406.

As described above, the human fatigue assessment device 400 determines the type of fatigue as to whether the fatigue is due to difficult work or due to monotonous work, based on the index values indicating the amount of parasympathetic nerve activity. The configuration described above allows to determining of the type of fatigue of the user, and to suitably assist to the user for recovery by switching a care (such as rest, sleep, and medicine) provided accordingly, for example. Furthermore, the human fatigue assessment device 400 is highly versatile since it extracts the amount of parasympathetic nerve activity using the electrocardiogram or pulse waves which are easy to measure, and determines the type of fatigue regardless of the scene.

In addition, this configuration allows to present the determination result of the type of fatigue to the user and to suitably assist the user's recovery by stimulating the user according to the type of fatigue.

Note that, when the human fatigue assessment device 400 does not include the device controller 405, the external devices may be controlled by an external structure.

Embodiment 3

FIG. 6 is a block diagram illustrating a configuration of the human fatigue assessment device 600 according to Embodiment 3 of the present invention. In FIG. 6, the same reference numerals may be assigned to the components identical to those in FIG. 4, and the description thereof may be omitted.

As illustrated in FIG. 6, the human fatigue assessment device 600 includes a physiological signal measuring unit 401, a feature value extracting unit 602, a storage unit 603, and a fatigue type determining unit 606, and further includes a checking unit 601 for checking whether the user is in an open-eye state or a closed-eye state. The human fatigue assessment device 600 may further include the device controller 405.

Through the potentiality demonstration experiments regarding the non-invasive assessment of human fatigue, the inventors found out that an α wave in the closed-eye state and a β wave in the open-eye state and in the closed-eye state extracted based on the brain signals (brain waves or magnetoencephalography) are related to the type of fatigue such as the fatigue due to difficult work and the fatigue due to monotonous work. More specifically, the inventors found out that the α wave in the closed-eye state significantly increases at the time of fatigue due to difficult work, and the beta wave in the open-eye state and the closed-eye state significantly decreases at the time of fatigue due to monotonous work.

Representative index values regarding the α wave includes as power values in α waveband (between 8 Hz and 13 Hz) in the power spectrum calculated by the frequency analysis of the time-series data of the brain signal (hereafter referred to as α). Alternatively, the index value regarding the α wave may be a Slow-wave Index in the closed-eye state (the value represented by the following formula 2) represented by a logarithm of α (the value represented by the following formula 1) or a logarithm of a power value in θ waveband (between 3 Hz and 8 Hz).

$$\ln \alpha \quad \text{(Formula 1)}$$

$$\ln \theta / \ln \alpha \quad \text{(Formula 2)}$$

Alternatively, the index values regarding the α wave may be % α calculated by dividing α by a total power value which includes α, θ, and a power value in β waveband (between 13 Hz and 25 Hz) (the value represented by the following formula 3), %θ calculated by dividing θ by the total power value (the value represented by the following formula 4), or Slow-wave Index in closed-eye state using % θ (the value represented by the following formula 5).

$$\% \alpha = \alpha/(\theta + \alpha + \beta) \quad \text{(Formula 3)}$$

$$\% \theta = \theta/(\theta + \alpha + \beta) \quad \text{(Formula 4)}$$

$$\% \theta / \% \alpha \quad \text{(Formula 5)}$$

The index value regarding the α wave may also be a value representing an α wave block suppressed by opening the eyes, which is one of the most distinctive characteristics of the α wave. For example, the index value regarding the α wave may be α-blocking (closed-eye–open-eye) which is a difference between α in the open-eye state (hereafter referred to as α (open)) and α in the closed-eye state (hereafter referred to as α (closed)), as shown in formula 6. Alternatively, the index value regarding the α wave may also be α blocking (closed-eye/open-eye) which is a ratio of α (closed) with respect to α (open), as shown in the following formula 7.

$$\alpha(\text{closed}) - \alpha(\text{open}) \quad \text{(Formula 6)}$$

$$\alpha(\text{closed})/\alpha(\text{open}) \quad \text{(Formula 7)}$$

The index value may also be a mean power frequency obtained by dividing the sum of a multiplied value of θ and the center frequency of the θ waveband, a multiplied value of α and the center frequency of the α waveband, and a multiplied value of β and the center frequency of the β waveband divided by the total power value (the value represented by the following formula 8).

$$(\theta \times 5.5 + \alpha \times 10.5 + \beta \times 19)/(\theta + \alpha + \beta) \quad \text{(Formula 8)}$$

Meanwhile, a representative index value regarding the β wave is a power value β in the β waveband (13 Hz or more and 25 Hz or less). Other index values regarding the β wave includes a logarithm of β (the value represented by the following formula 9, a slow-wave index in the open-eye state or closed-eye state (the value represented by the following formula 10), a slow-wave index in the open-eye state (the value represented by the following formula 11), % β (the value represented by the following formula 12), and a slow-wave index in the open-eye state or the closed-eye state (the value represented by the following formula 13).

$$\ln \beta \quad \text{(Formula 9)}$$

$$\ln \theta / \ln \beta \quad \text{(Formula 10)}$$

$$(\ln \alpha + \ln \theta)/\ln \beta \quad \text{(Formula 11)}$$

$$\% \beta = \beta/\theta + \alpha + \beta \quad \text{(Formula 12)}$$

$$\% \theta / \% \beta \quad \text{(Formula 13)}$$

Note that the methods of calculating % α indicated in the formula 3, % θ indicated in the formula 4, % β indicated in the formula 12, and the mean power frequency indicated in the formula 8 are not limited to the above-described formulas. For example, these values may be calculated using total power added with the power value in δ waveband (between 0 Hz and 3 Hz). However, there are many cases where the δ waveband, since it is largely affected by blinks.

The potentiality demonstration experiment regarding the non-invasive assessment of human fatigue performed by the inventors shall be described later in detail.

First, the operations of the human fatigue assessment device 600 shall be described as follows with reference to an example in which the logarithm of α is used as the index value.

First, the checking unit 601 generates checking information for checking whether the user is in the open-eye state or the closed-eye state. More specifically, the checking unit 601 checks whether the user is in the open-eye state or in the closed-eye state, using a camera and information such as an eye potential, and outputs the information as checking information to the physiological signal measuring unit 401. This checking information includes, for example, information which indicates 1 when in the open-eye state, and which indicates 0 when in the closed-eye state.

The physiological signal measuring unit 401 measures the brain signal of the user as the physiological signal, and adds the checking information to the measured physiological signal. More specifically, the physiological signal measuring unit 401 measures the brain wave among the brain signals of the user. Subsequently, when an input of the checking unit 601 is received, the physiological signal measuring unit 401 adds the checking information to the time-series data of the measured brain wave, and outputs the data obtained to the feature value extracting unit 602.

The feature value extracting unit 602 extracts the third feature value related to at least one of the β wave and the α wave obtained from the physiological signal measured by the physiological signal measuring unit 401. More specifically, the feature value extracting unit 602 extracts the third feature value using at least one of a power value in the β waveband and the power value in the α waveband in a time period during which the checking unit 601 determines that the user is in the open-eye state or in the closed-eye state.

For example, the feature value extracting unit 602 extracts the third feature value using the power value in the α waveband in a time period in which the checking unit 601 determines that the user is in the closed-eye state. The feature value extracting unit 602 also extracts the third feature value using the power value in the β waveband in a time period during which the checking unit 601 determines that the user is in the open-eye state or in the closed-eye state.

More specifically, the feature value extracting unit 602 performs a frequency analysis on the time-series data of the input wave, and calculates a frequency band corresponding to the α wave (between 8 Hz and 13 Hz) or a frequency band corresponding to the β wave (between 13 Hz and 25 Hz), and a power value (α or β). They may be a power value in a minimum time period necessary for the frequency analysis (for example, for 30 seconds), or may be a mean value of the power in a predetermined period (for example, for two minutes) obtained by collecting the calculated values in the minimum time periods in time-series. Subsequently, the feature value extracting unit 602 calculates ln α and ln β which are the logarithms of these values.

Furthermore, the feature value extracting unit 602 stores the calculated ln α and ln β in the storage unit 603 in time-series with the input checking information. Note that, as described above, there are various index values regarding the α wave and the β wave, and the index values are not limited to the logarithms of the power values.

The storage unit 603 is a memory for storing the third feature value extracted by the feature value extracting unit 602. More specifically, the storage unit 603 accumulates ln α or ln β in time-series each time the feature value extracting unit 602 outputs ln α or ln β.

The fatigue type determining unit 606 determines the type of fatigue of the user as to whether the fatigue is due to difficult work or the fatigue due to monotonous work, using the third feature value extracted by the feature value extracting unit 602. More specifically, the fatigue type determining unit 606 determines the type of fatigue by comparing any feature value among the third feature values extracted by the feature value extracting unit 602 and at least one of the third feature values stored in the storage unit 603.

More specifically, the fatigue type determining unit 606 determines the type of fatigue by comparing ln α or ln β which is attached with the identification information output from the feature value extracting unit 602 and ln α or ln β which is attached with the identification information stored in the storage unit 603. Note that, it is preferable that the fatigue type determining unit 606 uses the data to which the checking information indicating that the user is in the closed-eye state is attached. On the other hand, when ln β is used, the fatigue type determining unit 606 may use that data to which the information indicating either the open-eye state or the closed-eye state is attached.

For example, when the feature value extracting unit 602 extracts the third feature value using the power value in the α waveband in a time period during which the checking unit 601 determines that the user is in the closed-eye state, the fatigue type determining unit 606 determines that the fatigue is due to difficult work when the third feature value increases in time-series. Alternatively, when the feature value extracting unit 602 extracts the third feature value using the power value in the β waveband in a time period during which the checking unit 601 determines that the user is in the open-eye state or the closed-eye state, the fatigue type determining unit 606 determines that the fatigue is due to monotonous work when the third feature value decreases in time-series.

More specifically, when the feature value extracting unit 602 outputs ln α in the closed-eye state, the fatigue type determining unit 606 compares ln α in at one point before in time in time-series among ln α in the closed-eye state stored in the storage unit 603 and the ln α in the closed-eye state. This also applies to the case when using ln β in the open-eye state or in the closed-eye state. Note that, here, the fatigue type determining unit 606 compares the feature value at one point before in time in time-series and the current feature value. However, it is not limited to this example, and a comparison may be made between a feature value stored with the predetermined timing (for example, immediately after activation) as a reference value and the current feature value.

FIGS. 7A to 9B are flowcharts illustrating examples of determining type of fatigue by the fatigue type determining unit 606 according to Embodiment 3.

First, operation of the fatigue determining unit 606 illustrated in FIG. 7A shall be described. When the feature value extracting unit 602 outputs ln α in the closed-eye state (step S71), the fatigue type determining unit 606 calls ln α at one point before in time in time series, among ln α in the closed-eye state stored in the storage unit 603 (step S72).

Subsequently, the fatigue type determining unit 606 compares the two values, that is, the current ln α in the closed-eye state and ln α in the closed-eye state at one point before in time (step S73).

When the fatigue type determining unit 606 determines that the current ln α in the closed-eye state is larger than the ln α in the closed-eye state at one point before in time (Yes in step S73), the fatigue type determining unit 606 determines that the fatigue is due to difficult work (step S74).

When the fatigue type determining unit 606 determines that the current ln α in the closed-eye state is no larger than the ln α at one point before in time (No in step S73), the fatigue type determining unit 606 waits for the output of the next ln α from the feature value extracting unit 602, and repeats the operation from step S71, after the output of the next ln α.

The fatigue type determining unit 606 may also perform the operations illustrated in FIG. 7B. In this case, when the feature value extracting unit 602 outputs α-blocking (closed-eye/open-eye) (step S75), the fatigue type determining unit 606 calls α-blocking at one point before in time in time series, among α-blocking (closed-eye/open-eye) stored in the storage unit 603 (step S76).

The fatigue type determining unit 606 compares the two values, that is, the current α-blocking and the α-blocking at one point before in time (step S77).

When the fatigue type determining unit 606 determines that the current α-blocking is larger than the α-blocking at one point before in time (Yes in step S77), the fatigue type determining unit 606 determines that the fatigue is due to difficult work (step S78).

Alternatively, when the fatigue type determining unit 606 determines that the current α-blocking is no larger than the α-blocking at one point before in time (No in step S77), the fatigue type determining unit 606 waits for the next output of α-blocking by the feature value extracting unit 602, and repeats the operations from step S81 after the output of the next α-blocking.

The fatigue type determining unit 606 may also perform the operations illustrated in FIG. 8A. In this case, when the feature value extracting unit 602 outputs ln α and ln θ/ln α (hereafter referred to as a feature value) in the closed-eye state (step S81), the fatigue type determining unit 606 calls an α feature value in the closed-eye state at one point before in time in time-series, among the α feature values in the closed-eye state stored in the storage unit 603 (step S82).

Subsequently, the fatigue type determining unit 606 compares the two values; that is, the current ln α in the closed-eye state and ln α at one point before in time in closed-eye state (step S83).

First, when the fatigue type determining unit 606 determines that the current ln α in the closed-eye state is larger than the ln α at one point before in time in closed-eye state (Yes in step S83), the fatigue type determining unit 606 compares the current ln θ/ln α in the closed-eye state and ln θ/ln α at one point before in time in the closed-eye state (step S84).

When the fatigue type determining unit 606 determines that the current ln θ/ln α is smaller than ln θ/ln α at one point before in time in the closed-eye state (Yes in step S84), the fatigue type determining unit 606 determines that the fatigue is due to difficult work (step S85).

When the current ln α in the closed-eye state is no larger than ln α in the closed-eye state at one point before in time (No in step S83), the fatigue type determining unit 606 waits for the feature value extracting unit 602 until an output of the next α feature value, and repeats the operations from step S81 after the output of the next α feature value.

When the fatigue type determining unit 606 determines that the current ln θ/ln α in the closed-eye state is no smaller than the ln θ/ln α at one point before in time in the closed-eye state (No in step S84), the fatigue type determining unit 606 repeats the operation from step S81 after the output of the next α feature value.

Alternatively, the fatigue type determining unit 606 may be configured to perform operations illustrated in FIG. 8B. In this case, when the feature value extracting unit 602 outputs ln α and a mean frequency (step S86), the fatigue type determining unit 606 calls ln α and a mean frequency at one point before in time in time-series in the closed-eye state stored in the storage unit 603 (step S87).

The fatigue type determining unit 606 compares the two values; that is, the current mean frequency in the closed-eye state and the mean frequency at one point before in time in the closed-eye state (step S88).

When there is no change in the frequency band including the mean frequency of the two values (for example, θ waveband, α waveband, and β waveband) (Yes in step S88), the fatigue type determining unit 606 compares the current ln α in the closed-eye state and the ln α at one point before in time in the closed-eye state (step S83).

When the fatigue type determining unit 606 determines that the current ln α is larger than the ln α at one point before in time (Yes in step S83), the fatigue type determining unit 606 determines that the fatigue is due to difficult work (step S89).

When the fatigue type determining unit 606 determines that there is a change in the frequency band including the mean frequency in step S88 (No in step S88) and when it is determined that the current ln α is no larger than the ln α at one point before in time (No in step S83), the fatigue type determining unit 606 waits for the output of the next feature value, and repeats the operation from step S86 after the output.

Subsequently, the operation of the fatigue type determining unit 606 illustrated in FIG. 9A shall be described. Here, when the feature value extracting unit 602 outputs ln β in the open-eye state (step S91), the fatigue type determining unit 606 calls ln β at one point before in time in time-series in the open-eye state, among ln β in the open-eye state stored in the storage unit 603 (step S92).

Subsequently, the fatigue type determining unit 606 compares the two values; that is, the current ln β in the open-eye state and ln β at one point before in time (step S93).

When the fatigue type determining unit 606 determines that the current ln β in the open-eye state is smaller than ln β at one point before in time in the open-eye state (Yes in step S93), the fatigue type determining unit 606 determines that the fatigue is due to monotonous work (step S94).

When the fatigue type determining unit 606 determines that the current ln β in the open-eye state is no smaller than the ln β at one point before in time in the open-eye state (No in step S93), the fatigue type determining unit 606 waits until the feature value extracting unit 602 outputs the next ln β, and repeats the operation from step S91 after the output of the next ln β.

Note that, the feature value extracting unit 602 may extract ln β in the closed-eye state, and perform the same process in the fatigue type determining unit 606. In this case, in the same manner as the process in step S93, the fatigue type determining unit 606 determines whether or not the fatigue is due to monotonous work, based on whether or not the current ln β is smaller than the ln β at one point before in time.

Figure 9B:
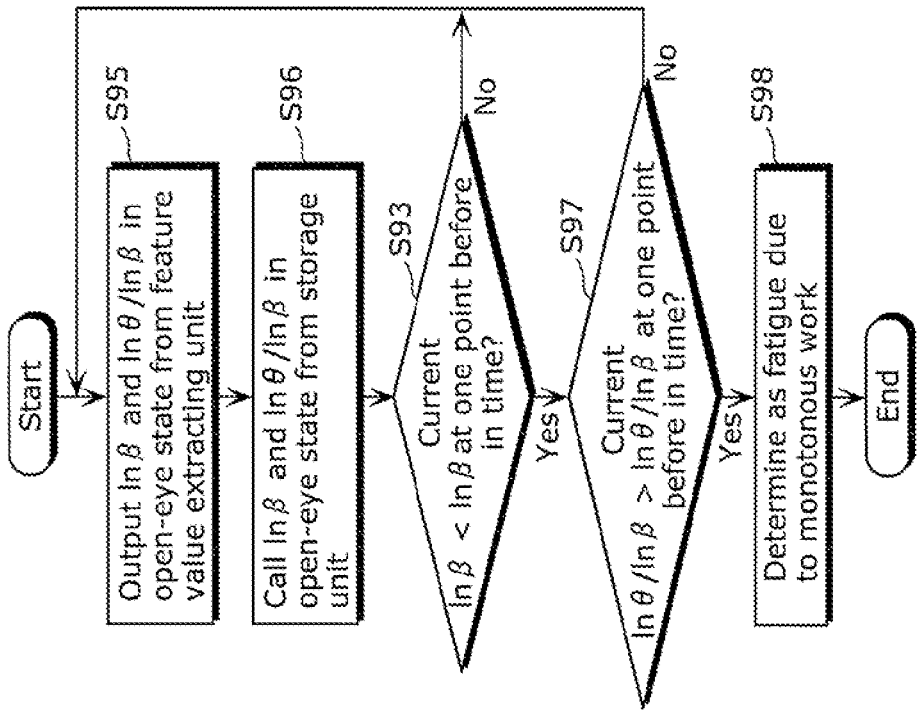
FIG. 9B is a flowchart illustrating another example of determining a type of fatigue by the fatigue type determining unit using a power value in β band frequency according to Embodiment 3.
Figure 9A:
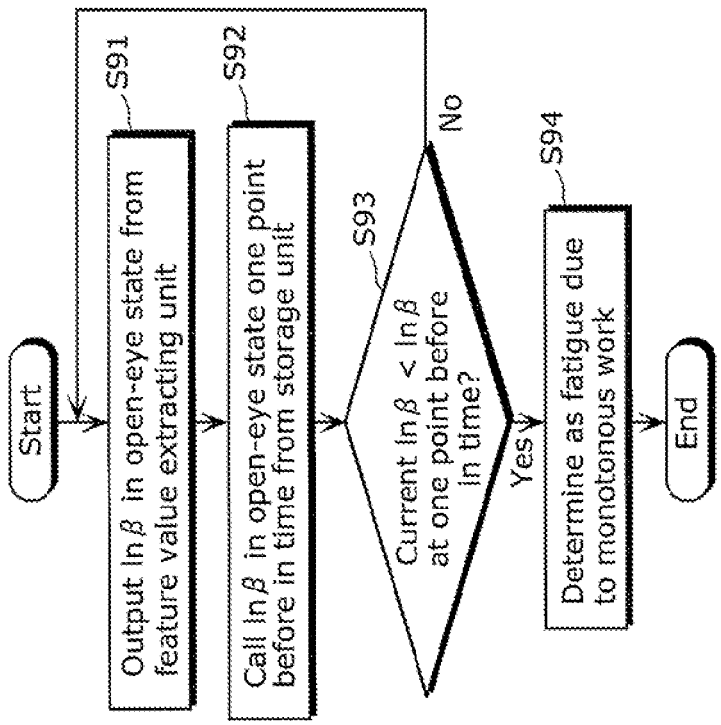
FIG. 9A is a flowchart illustrating an example of determining a type of fatigue by a fatigue type determining unit using a power value in β band frequency according to Embodiment 3.

Furthermore, the fatigue type determining unit 606 may have a configuration to perform the operations illustrated in FIG. 9B. In this case, when the feature value extracting unit 602 outputs ln β and ln θ/ln β in the open-eye state (hereafter referred to as β feature value) (step S95), the fatigue type determining unit 606 calls the β feature value at one point before in time in time-series in the open-eye state, among the β feature values in the open-eye state stored in the storage unit 603 (step S96).

Subsequently, the fatigue type determining unit 606 compares the two values; the current ln β in the open-eye state, and the ln β at one point before in time (step S93).

First, when the fatigue type determining unit 606 determines that the current ln β in the open-eye state is smaller than ln β at one point before in time in the open-eye state (Yes in step S93), the fatigue type determining unit 606 compares the current ln θ/ln β in the open-eye state and the ln θ/ln β at one point in time before in the open-eye state (step S97).

When the fatigue type determining unit 606 determines that the ln θ/ln β in the open-eye state is larger than the ln θ/ln β at one point before in time (Yes in step S97), the fatigue type determining unit 606 determines that the fatigue is due to monotonous work (step S98).

When the fatigue type determining unit 606 determines that the current ln β in the open-eye state is no larger than the ln β in the open-eye state at one point before in time (No in step S93), the fatigue type determining unit 606 waits until the feature value extracting unit 602 outputs the next β feature value, and repeats the operations from step S95 after the output of the next feature value.

Furthermore, when the fatigue type determining unit 606 determines that the current ln θ/ln β in the open-eye state is no larger than ln θ/ln β at one point before in time in open-eye state (No in step S97), the fatigue type determining unit 606 also repeats the operations from step S95 after the output of the next β feature value.

Note that, the feature value extracting unit 602 may extract the β feature value in the closed-eye state, and the fatigue type determining unit 606 may perform the same process. In this case, in the same manner as the process in steps S93 and S97, the fatigue type determining unit 606 determines whether or not the fatigue is due to monotonous work, based on whether or not the current ln β is smaller than the ln β at one point before in time, and whether or not the current ln θ/ln β is larger than the ln θ/ln β at one point before in time.

In the description above, the case in which the fatigue is determined to be due to difficult work and the case in which the fatigue is determined to be due to monotonous work are described separately. However, the combination of the cases allows determination of the type of fatigue using the brain signals, as to whether the fatigue is due to difficult work or monotonous work.

As described above, the human fatigue assessment device 600 can determine the type of fatigue as to whether the fatigue is due to difficult work or monotonous work, based on the feature value related to at least one of the β wave and the α wave from the brain signal. Based on the determined type of fatigue, it is possible to support the user for recovery more suitably by switching care provided to the user (such as rest, sleep, medicine), for example. Furthermore, the human fatigue assessment device 600 can determine the type of fatigue from the brain signal measured by contacting the head with a sensor. Thus, human fatigue assessment device 600 can be applied to people wearing hats or headset microphones at work, for example.

In addition, with this configuration, at least one of the power values in the β waveband or in the α waveband are used, and a value when the user is in the open-eye state and a value when the user is in the closed-eye state are distinguished. Thus, it is possible to further improve the accuracy of the fatigue assessment.

Furthermore, with this configuration, whether or not the fatigue of the user is due to difficult work is determined based on the power value in the α waveband in the time period in which the user is determined to be in the closed-eye state. Thus, it is possible to further improve the accuracy of the fatigue assessment. In addition, it is possible to support the user for recovery more suitably from the fatigue due to difficult work by determining the type of fatigue.

Furthermore, with this configuration, whether or not the user's fatigue is due to monotonous work is determined from a power value in the β waveband in a time period in which the user is determined to be in the open-eye state or in the closed-eye state. Thus, it is possible to improve the accuracy of the fatigue assessment. In addition, determining the type of fatigue enables assistance to the user for recovery from the fatigue due to monotonous work.

Furthermore, with this configuration, it is possible to present the result of determination of the type of fatigue to the user or to assist the user in a way suitable for the user, by stimulating the user according to the type of fatigue.

Note that, when the human fatigue assessment device 600 does not have a device controller 405, external devices may be controlled by an outside structure.

Embodiment 4

Figure 10:
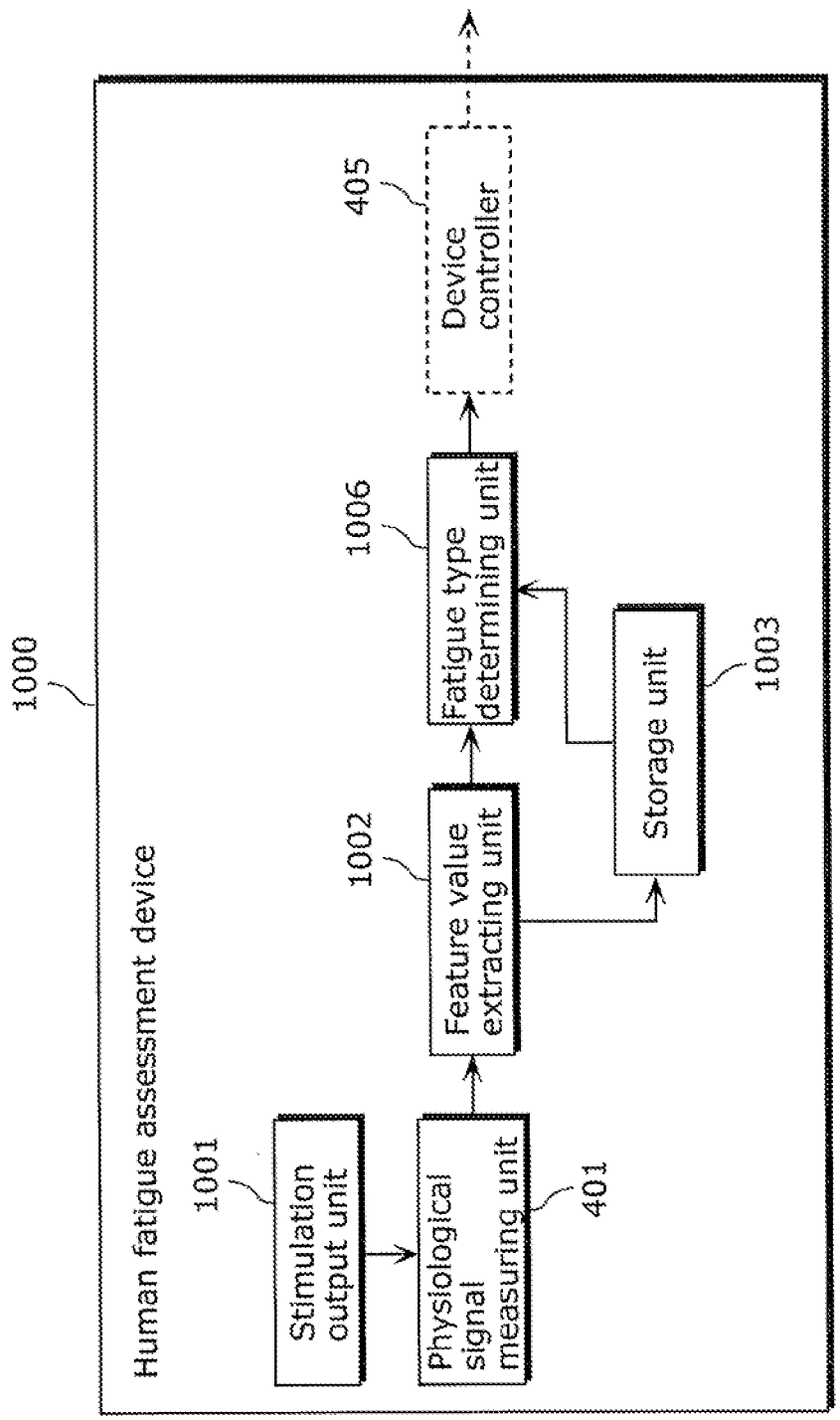
FIG. 10 is a block diagram illustrating a configuration of a human fatigue assessment device according to Embodiment 4.

FIG. 10 is a block diagram illustrating a configuration of the human fatigue assessment device 1000 according to Embodiment 4 of the present invention. In FIG. 10, the same reference numerals may be assigned to the components identical to those in FIG. 4, and the description thereof may be omitted.

As illustrated in FIG. 10, the human fatigue assessment device 1000 includes a physiological signal measuring unit 401, a feature value extracting unit 1002, a storage unit 1003, and a fatigue type determining unit 1006, and further includes a stimulation output unit 1001 which outputs audio stimulation to the user. The human fatigue assessment device 1000 may further include the device controller 405.

Through a potentiality demonstration experiment regarding the non-invasive assessment of human fatigue, the inventors found out that the changes in the feature values in the accelerated plethysmogram waveform in response to tone-burst stimuli (90 dB at 1000 Hz) differ depending on the type of fatigue.

More specifically, the inventors found out that the feature values related to accelerated plethysmogram waveform in response to audio stimulation significantly change even after a mental fatigue stress involving monotonous work, but does not significantly change after a fatigue stress involving difficult work. To put it differently, pulse wave response to the audio stimulation slows down at the time of fatigue due to difficult work.

Here, the feature value related to the accelerated plethysmogram waveform may be feature values using information of accelerated plethysmogram waveform components, including the information of the c wave or the d wave, as described in Embodiment 1. The potentiality demonstration experiment regarding the non-invasive assessment of human fatigue performed by the inventors shall be described later in detail.

Here, the following description shall be made using an example in which the physiological signal measuring unit 401 measures pulse waves, and the feature value extracting unit 1002 extracts c/a value which is a peak ratio of the c wave and the a wave.

The stimulation output unit 1001 outputs, to the user, the audio stimulation which stimulates the auditory sense of the user. More specifically, the stimulation output unit 1001 outputs the audio stimulation to the user, and outputs stimulation information indicating the output of the audio stimulation to the physiological signal measuring unit 401.

Here, the audio stimulation output to the user may be audio stimuli which are 90 dB at 1000 Hz, which is frequently used for clinical trials in medical field. Note that, the stimulation information is 1 when outputting the audio stimulation, and is 0 when not outputting the audio stimulation, for example.

The physiological signal measuring unit 401 measures the pulse signals of the user, and when receiving the stimulation information from the stimulation output unit 1001, the physiological signal measuring unit 401 attaches the stimulation information to the time-series data of the measured pulse wave signal, and outputs the signal to the feature value extracting unit 1002.

The feature amount extracting unit 1002 extracts a first feature value obtained from the systolic posterior component of the pulse wave signal measured by the physiological signal measuring unit 401. More specifically, the feature value extracting unit 1002 calculates the accelerated plethysmogram from the pulse wave signal, and extract a ratio of the peak value of the c wave with respect to the peak value of the a wave of the accelerated plethysmogram as a first feature value.

More specifically, first, the feature amount extracting unit 1002 converts the pulse wave signals measured by the physiological signal measuring unit 401 to an accelerated plethysmogram waveform, by obtaining a second order differential of the pulse signal. In particular, a c/a value which is a ratio of the c wave corresponding to the systolic posterior component of the accelerated plethysmogram and the a wave corresponding to the systolic anterior component is calculated, among the accelerated plethysmogram waveform component, and outputs the c/a value to the storage unit 1003 with the stimulation information.

The storage unit 1003 stores the first feature amount extracted from the feature value extracting unit 1002 in time-series. Note that, the feature amount extracting unit 1002 may output a value for one beat of pulse wave signal without any modification, or output an average value within a predetermined time period (for example, 10 seconds).

The fatigue type determining unit 1006 determines the type of fatigue of the user whether it is the fatigue due to difficult work or monotonous work, using the third feature value extracted by the feature amount extracting unit 1002.

More specifically, the fatigue type determining unit 1006 determines the first feature value stored in the storage unit 1003 in a time period before the stimulation output unit 1001 outputs audio stimulation in the time period before the stimulation output unit 1001 outputs the audio stimulation, and the first feature value in a time period when the stimulation output unit 1001 outputs the audio stimulation.

More specifically, the fatigue type determining unit 1006 determines that the fatigue is due to monotonous work when the first feature values stored in the storage unit 1003 in the time period when the stimulation output unit 1001 outputs the audio stimulation increases with respect to the first feature value stored in the storage unit 1003 in the time period before the stimulation output unit 1001 outputs the audio stimulation, and determines that the fatigue is due to difficult work when the first feature value does not increase.

More specifically, the fatigue type determining unit 1006 determines the type of fatigue by comparing the c/a value to which no stimulation information is attached and the c/a value to which the stimulation information is attached to determine the type of fatigue. When the feature value extracting unit 1002 outputs a new c/a value with stimulation information attached, the fatigue type determining unit 1006 calls a c/a value to which no stimulation information is attached, at one point before in time in time-series, among the c/a values stored in the storage unit 1003, and compares with the current c/a value to which the stimulation information is attached.

Certainly, the determination of the type of the fatigue determined by the fatigue type determining unit 1006 is not limited to this example. For example, the comparison with the current c/a value to which the stimulation information is attached, using a c/a value to which no stimulation information is attached stored with a predetermined timing (for example, immediately after the activation) as a reference value.

Figure 11:
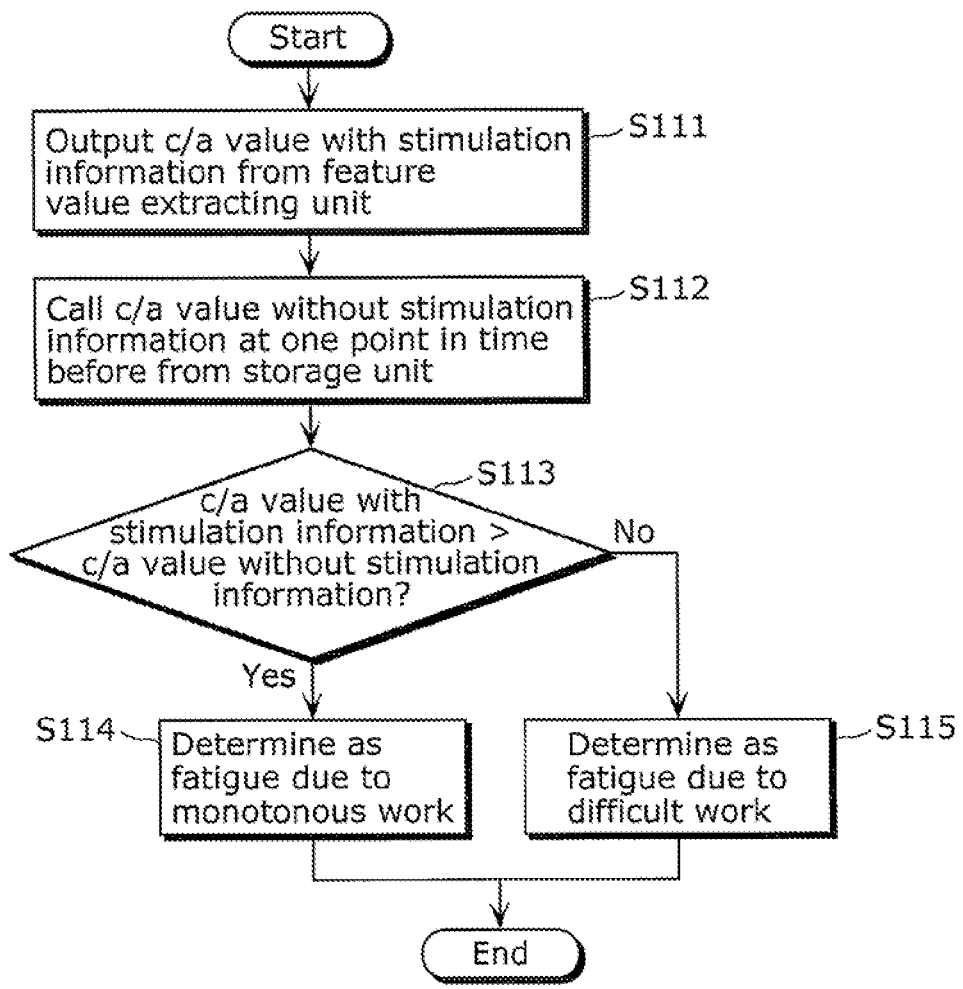
FIG. 11 is a flowchart illustrating an example of determining a type of fatigue by a fatigue type determining unit according to Embodiment 4.

FIG. 11 is a flowchart illustrating an example of determination on the type of fatigue by the fatigue type determining unit 1006 in Embodiment 4.

As illustrated in FIG. 11, when the feature value extracting unit 1002 outputs a c/a value to which stimulation information is attached (step S111), the fatigue type determining unit 1006 calls a c/a value to which no stimulation information is attached at one point before in time in time-series, among the c/a values stored in the storage unit 1003 (step S112).

The fatigue type determining unit 1006 compares the two values, that is, the current c/a value to which stimulation information is attached and the c/a value at one point before in time to which the stimulation information is no attached (step S113).

When the fatigue type determining unit 1006 determines that the current c/a value to which the stimulation information is attached is larger than the c/a value at one point before in time to which no stimulation information is attached (Yes in step S113), the fatigue type determining unit 1006 determines that the fatigue is due to monotonous work (step S114).

Furthermore, when the fatigue type determining unit 1006 determines that the current c/a value to which the stimulation information is attached is no larger than the c/a value at one point before in time to which no stimulation information is attached (No in step S113), the fatigue type determining unit 1006 determines that the fatigue is due to difficult work (step S115).

As such, the human fatigue assessment device 1000 determines the type of fatigue of the user, that is, whether the fatigue is due to difficult work or monotonous work, from the change in feature values related to the accelerated plethysmogram waveform in response to audio stimulation. The configuration described above allows to determine the type of fatigue of the user, and to suitably assist to the user for recovery by switching a care (rest, sleep, medicine, and others) provided accordingly, for example. In addition, the human fatigue assessment device 1000 is highly versatile regardless of situations, since the type of fatigue is determined, using pulse wave which can be easily measured and audio stimulations that does not require a special device. For example, the pulse waves can be measured from the part in contact with the driver during driving, and the type of fatigue can be determined using the change in the pulse wave signals in response to the audio stimulation output from a car navigation system. That is, an application to a driving monitoring device is possible.

Embodiment 5

Figure 12:
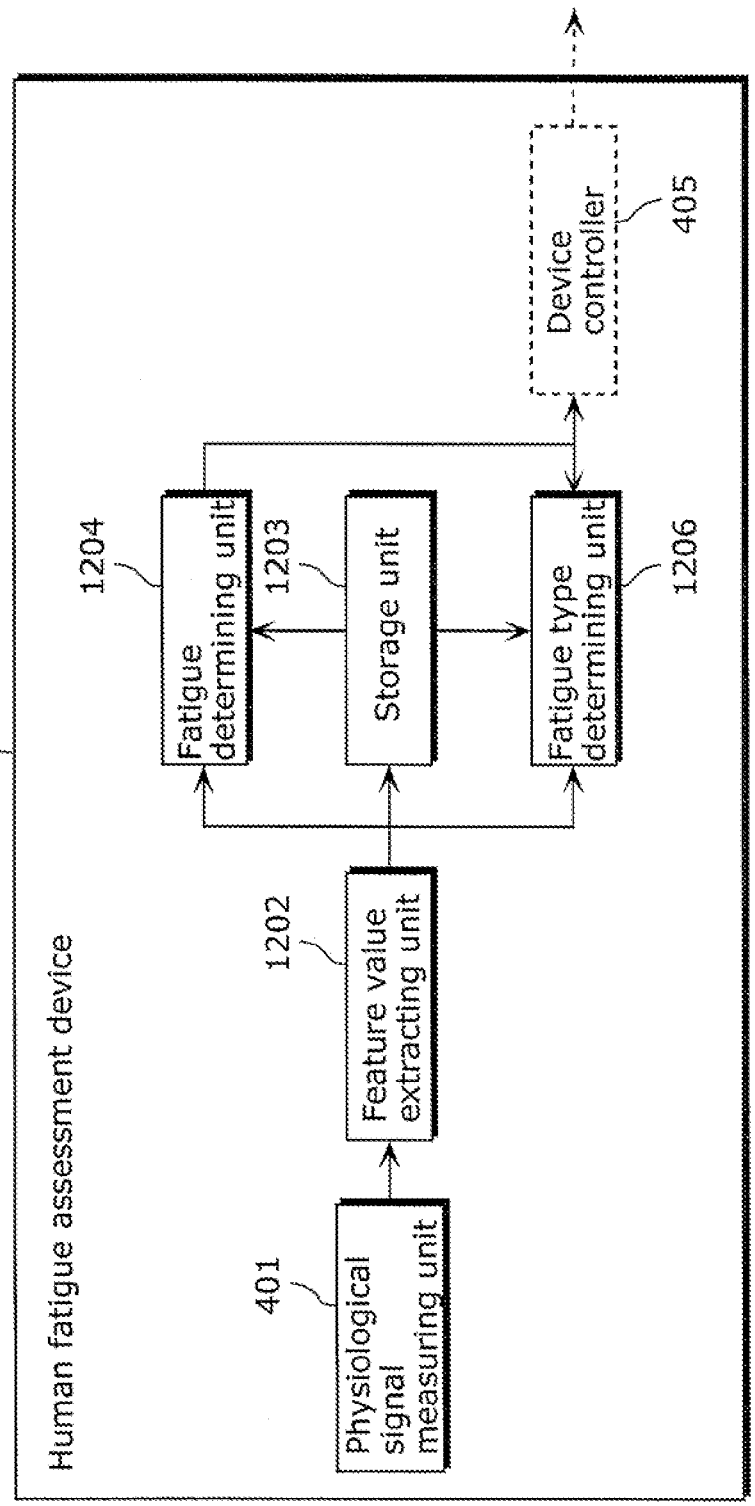
FIG. 12 is a block diagram illustrating a configuration of a human fatigue assessment device according to Embodiment 5.

FIG. 12 is a block diagram illustrating the configuration of the human fatigue assessment device 1200 according to Embodiment 5 of the present invention. In FIG. 12, the same reference numerals may be assigned to the components identical to those in FIG. 4, and the description thereof shall be omitted.

As illustrated in FIG. 12, the human fatigue assessment device 1200 includes a physiological signal measuring unit 401, a feature value extracting unit 1202, a storage unit 1203, and a fatigue type determining unit 1206, and further includes a fatigue determining unit 1204 which determines whether or not the user is fatigued. The human fatigue assessment device 1200 may further include the device controller 405.

Here, the following describes the operations of the human fatigue assessment device 1200, using an example in which the pulse wave signals are measured by the physiological signal measuring unit 401.

When the physiological signal measuring unit 401 measures the pulse wave signal, the feature value extracting unit 1202 extracts a c/a value in the same manner as Embodiment 1, and a HF power value in the same manner as Embodiment 2. Here, with regard to the c/a value, the feature value extracting unit 1202 may output a value of one beat of the pulse wave signal without any modification, or may output a mean value in the same time period (for example, for 30 seconds) as a minimum time period of the HF power value.

The storage unit 1203 stores, in time-series, the c/a values and the HF power values extracted by the feature value extracting unit 1202.

The fatigue determining unit 1204 determines whether or not the user is fatigued, in the same manner as Embodiment 1.

When the fatigue determining unit 1204 determines that the user is fatigued, the fatigue type determining unit 1206 determines the type of the fatigue of the user as to whether the fatigue is due to difficult work or monotonous work, in the same manner as Embodiment 2.

Figure 13:
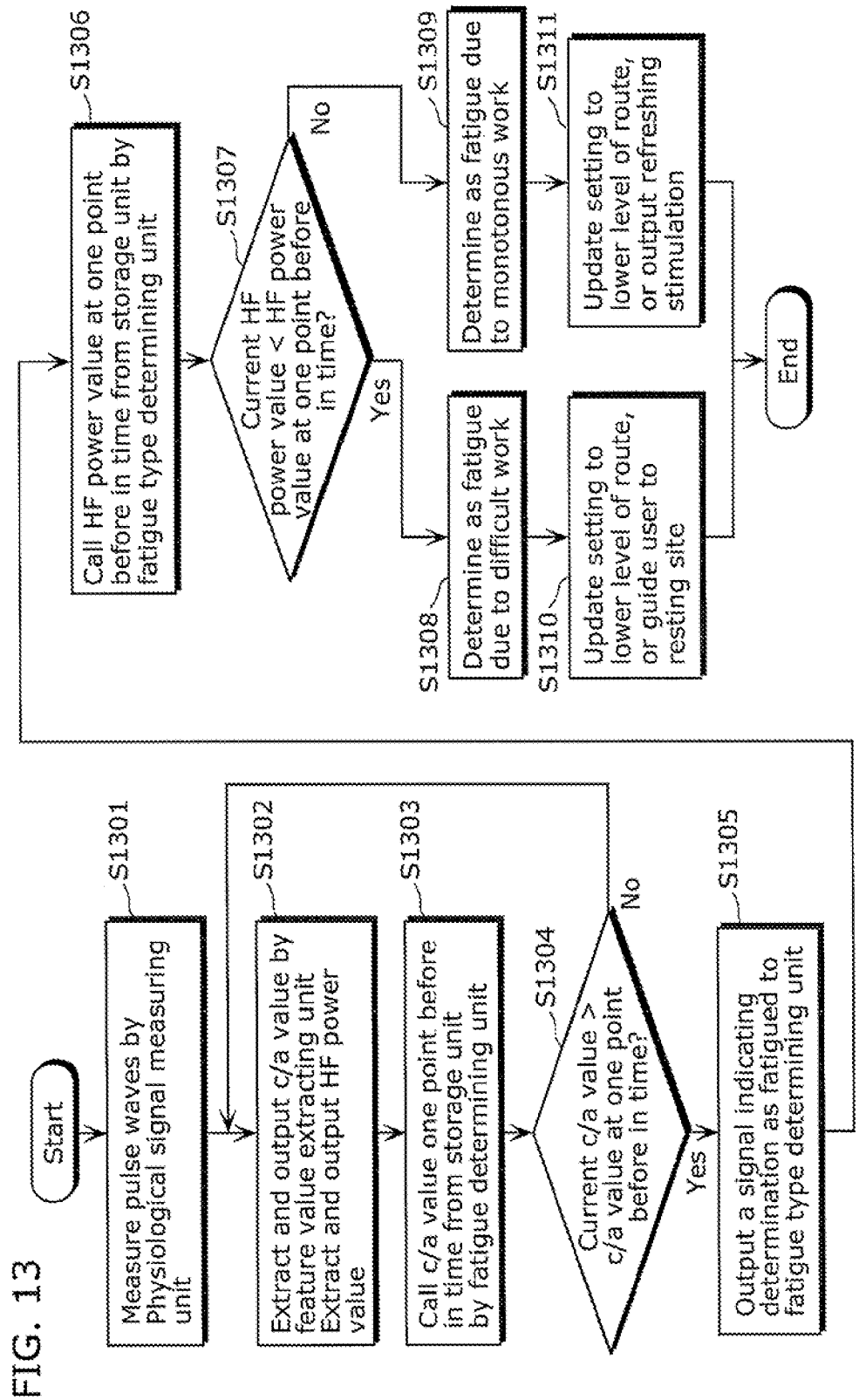
FIG. 13 is a flowchart illustrating an example of operations of the human fatigue assessment device according to Embodiment 5.

FIG. 13 is a flowchart illustrating an example of the operations by the human fatigue assessment device 1200 according to Embodiment 5.

More specifically, FIG. 13 is a flowchart illustrating the processes when the human fatigue assessment device 1200 is applied when the user is driving a vehicle. Here, the physiological signal measuring unit 401 may be a living body sensor incorporated in the steering component, or a wearable living body sensor attached to an appropriate part of the driver, for example, fingers or ears.

As illustrated in FIG. 13, when the physiological signal measuring unit 401 measures the pulse wave (step S1301), the feature value extracting unit 1202 extracts and outputs the c/a values and the HF power values (step S1302).

When the feature value extracting unit 1202 outputs the c/a value, the fatigue determining unit 1204 calls a c/a value at one point before in time-series, among the c/a values stored in the storage unit 1203 (step S1303).

Subsequently, the fatigue determining unit 1204 compares the two values, that is, the current c/a value and the c/a value at one point before in time (step S1304).

When the fatigue determining unit 1204 determines that the current c/a value is larger than the c/a value at one point before in time (Yes in step S1304), the fatigue determining unit 1204 determines that the user is fatigued, and outputs a signal indicating that the determination is made as the user being fatigued to the fatigue type determining unit 1206 (step S1305). Here, the output signal indicating the fatigue determination may be 1 when the user is fatigued, and 0 in other cases.

Alternatively, when the fatigue determining unit 1204 determines that the current c/a value is no larger than the c/a value at one point before in time (No in step S1304), the fatigue determining unit 1204 waits until the feature value extracting unit 1202 outputs the next c/a value and HF power value, and repeats the operations from step S1302 after the next output of the c/a value and the HF power value.

Next, when the fatigue type determining unit 1206 receives a signal from the fatigue determining unit 1204 indicating that the user is fatigued, the fatigue type determining unit 1206 calls a HF power value at one point before in time in time-series, among the HF power values stored in the storage unit 1203 (step S1306).

Subsequently, the fatigue type determining unit 1206 compares the two values, that is, the current HF power value and the HF power value at one point before in time (step S1307).

When the current HF power value is smaller than the HF power value at one point before in time (Yes in step S1307), the fatigue type determining unit 1206 determines that the fatigue is due to difficult work (step S1308).

On the other hand, when the fatigue type determining unit 1206 determines that the current HF power value is no smaller than the HF power value at one point before in time (No in step S1307), the fatigue type determining unit 1206 determines that the fatigue is due to monotonous work (step S1309).

Next, when the fatigue type determining unit 1206 outputs the determination result that the fatigue is due to difficult work, the device controller 405 controls a device to execute assistance function, such as lowering the difficulty of the route set in the car navigation system, or guiding the car to a safe stop and prompting the user to take a rest (step S1310).

On the other hand, when the fatigue type determining unit 1206 outputs a determination result indicating that the fatigue is due to monotonous work, the device controller 405 controls the device to execute assistance functions such as switching the route set in the car navigation system to a less monotonous route, outputting refreshing scent, heat, or air current stimulation, or increasing the speed of the beat or tempo of music (step S1311).

Here, the fatigue determining unit 1204 determines whether or not the user is fatigued based on the feature values related to the pulse waves, and the fatigue type determining unit 1206 determines the type of fatigue based on the feature value related to the parasympathetic nerve activity. However, it is not limited to this example. The fatigue determining unit 1204 may further determine whether the user is fatigued, using the feature values related to brain waves, or the fatigue type determining unit 1206 may determine the type of fatigue in the same manner as Embodiment 3 or Embodiment 4.

As described above, the human fatigue assessment device 1200 determines whether or not the user is fatigued, and determines the type of the fatigue as to whether the fatigue is due to difficult work or monotonous work, based on the feature values related to pulse wave, and the feature values related to the amount of parasympathetic nerve activity, which is one of the autonomous nerve activity. With this configuration, it is possible to reduce the influence of the factors other than fatigue, and improve the accuracy of the determination as to whether or not the user is fatigued, and the accuracy of the determination on the type of fatigue. Furthermore, it is possible to support the user for recovery in a more suitable way, by switching the care provided to the user according to the determination result of the type of fatigue.

(Variations)

Note that, although the present invention has been described based on the embodiments above, the present invention is not limited to the embodiments, and includes other cases as follows.

(1) When all or part of the devices are configured with a computer system including microprocessor, ROM, RAM, and hard disk unit, a computer program for implementing the operations identical to the operations by the devices is stored in the RAM or the hard disk unit. When the microprocessor operates according to the computer program, the devices achieve their functions.

(2) A part or all of the constituent elements constituting the respective apparatuses may be configured from a single System-LSI (Large-Scale Integration). The System-LSI is a super-multi-function LSI manufactured by integrating constituent units on one chip, and is specifically a computer system configured by including a microprocessor, a ROM, a RAM, and so on. A computer program capable of achieving the operations equivalent to those by the devices is stored in the RAM. When the microprocessor operates according to the computer system, the system LSI achieves its function.

(3) A part or all of the constituent elements constituting the respective apparatuses may be configured as an IC card which can be attached and detached from the respective apparatuses or as a stand-alone module. The IC card or the module is a computer system configured from a microprocessor, a ROM, a RAM, and so on. The IC card or the module may also be included in the aforementioned super-multi-function LSI. The IC card or the module achieves its function through the microprocessor's operation according to the computer program. The IC card or the module may also be implemented to be tamper-resistant.

(4) The present invention may be a method implemented by the process by the computer described above. In addition, the present invention may be a computer program for realizing the previously illustrated method, using a computer, and may also be a digital signal including the computer program.

Furthermore, the present invention may also be realized by storing the computer program or the digital signal in a computer readable recording medium. The computer readable recording medium includes flexible disc, a hard disk, a CD-ROM, an MO, a DVD, a DVD-ROM, a DVD-RAM, a BD (Blu-ray Disc), and a semiconductor memory, for example. Furthermore, the present invention may be the digital signals stored in the recording medium.

Furthermore, the present invention may also be realized by the transmission of the aforementioned computer program or digital signal via a telecommunication line, a wireless or wired communication line, a network represented by the Internet, a data broadcast and so on.

The present invention may also be a computer system including a microprocessor and a memory, in which the memory stores the aforementioned computer program and the microprocessor operates according to the computer program.

Furthermore, by transferring the program or the digital signal by recording onto the aforementioned recording media, or by transferring the program or digital signal via the aforementioned network and the like, execution using another independent computer system is also possible.

(5) Arbitrary combination of the aforementioned modifications and embodiment is included within the scope of this invention.

Example 1

Embodiments 1 to 5 are based on the findings by the inventors through a trial involving participants for validation of the capability of the non-invasive human fatigue assessment. The findings include different correlations among the change in electrocardiograms, accelerated plethysmograms, brain waves, and magnetoencephalography when human is in fatigue (fatigued) or in the middle of fatigue, depending on whether the fatigue is due to difficult work or due to monotonous work.

The following shall describe the experiments involving participant in detail, but the experiments are not limited to this example.

<Checking Validity of Mental Fatigue Stress>

(1) Experiment Design

The inventors performed a mental fatigue stress test by performing two N-back tests using personal computers (PC) for 30 minutes on 20 healthy adults (male, age 32.0±10.2 (mean±standard deviation)) as test subjects, and a performance assessment (measuring total trials and total errors when performing the task) by Advanced Trail Making Test (ATMT) before and after the test for 30 minutes.

Before and after ATMT, subjective tests were performed. The test includes measuring total fatigue, mental fatigue, physical fatigue, stress, motivation, sleepiness, difficulty, monotonousness, and boredom based on the Visual Analog Scale (VAS), and sleepiness based on Karolinska Sleepiness Scale (KSS). Two tests were performed as crossover to eliminate the influence of the order of the tests performed.

(2) Method of Mental Fatigue Test

Among the N-back tests, 0-back test and 2-back test were used. The 0-back test lets the user to determine whether a specified number, character, or sign is displayed without using his working memory, and forces the test subjects to perform monotonous work.

The inventors intended to cause the fatigue due to monotonous work on the test subjects by continuously performing this test for 30 minutes. More specifically, the work involves clicking the right-button of the PC mouse when the specified number, character, or sign is displayed on the PC screen, and clicking the left-button of the PC mouse in other cases.

The 2-back test lets the test subjects to determine whether the currently displayed number, character, or sign is the same as the number, character, or sign displayed two times before, while using his working memory, and forces the user to perform difficult work.

The inventors intended to cause the fatigue due to difficult work on the test subjects by continuously performing this test for 30 minutes. More specifically, the work involves clicking the right button of the PC mouse when the number, character, or sign displayed on the PC screen is the same as the number, character, or sign displayed two times before, and clicking the left-button of the PC mouse in other cases. Numbers, characters, or signs were displayed for 0.5 seconds, and the interval after numbers, characters, or signs disappears to the next display was 2.5 seconds.

(3) Results

Figure 14:
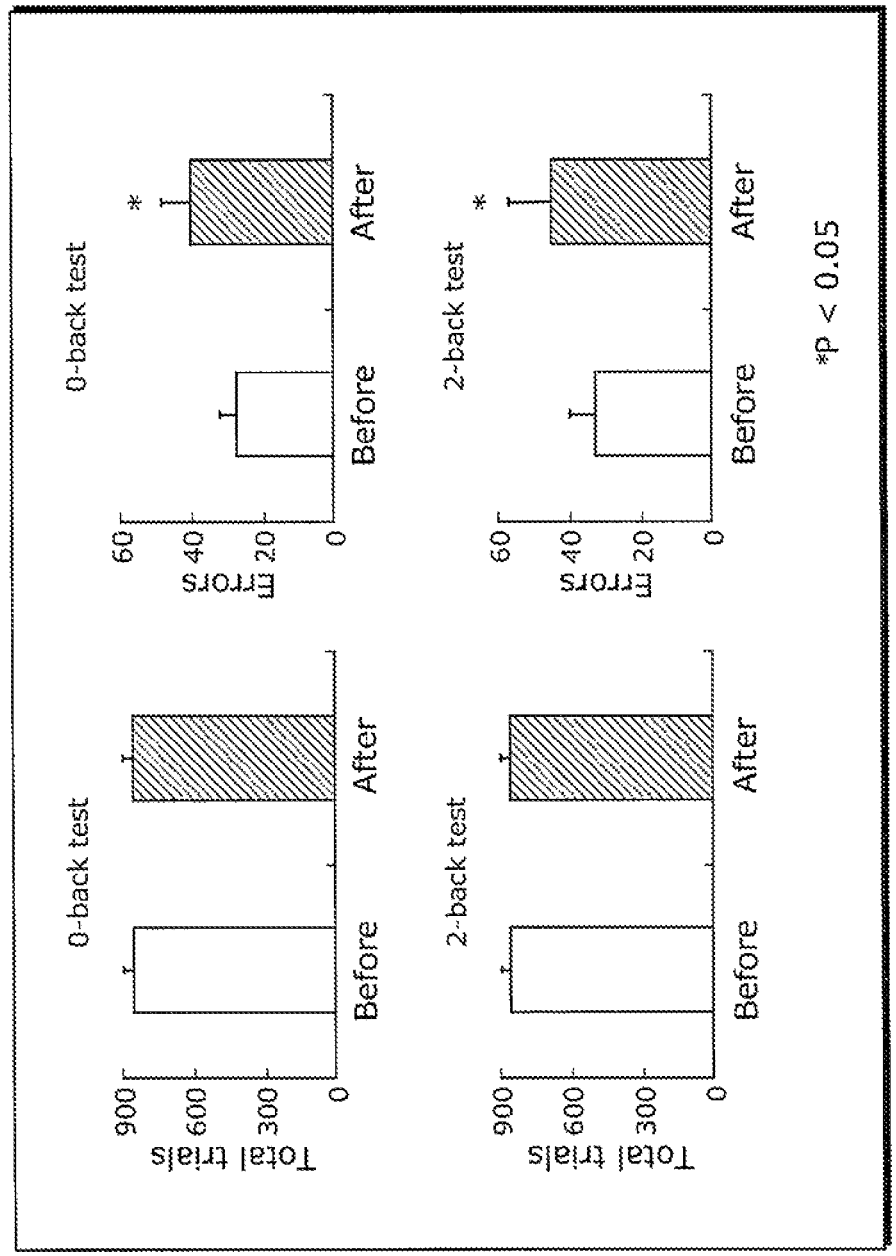
FIG. 14 illustrates changes in scores of ATMT before and after mental fatigue stress.

FIG. 14 illustrates changes in scores of ATMT before and after mental fatigue stress.

The results of the ATMT before and after the mental fatigue stress test were evaluated to determine whether the N-back test for 30 minutes induces fatigue. The evaluation indicates significant increase in the number of errors in both a 0-back tested group and a 2-back tested group. Note that it has been checked that there is no significant change in the number of errors in ATMT before and after a 30-minutes relaxing task.

Here, "*P<0.05" indicates that the number of errors increased in the graphs with * in the figure, satisfying a statistical significance level of 5%. Note that, the detailed description in the other diagrams is omitted, since the same applies to the other diagrams as well.

FIG. 15A illustrates subjective report scores before and after the mental fatigue stress.

The results of the VAS scores indicating total fatigue and mental fatigue before and after the mental fatigue stress indicates significant increases in both the 0-back tested group and the 2-back tested group. Accordingly, the decrease in the mental performance and increase in the feeling of fatigue were indicated after the N-back test for 30 minutes. Thus, the 30-minutes N-back test is suitable as the stress test.

In addition, FIG. 15B indicates subjective report scores at the time of N-back test, recorded after the end of the test.

The subjective test at the time of N-back test recorded after the end of the test indicates significant higher values in mental fatigue and difficulty VAS scores, compared to the 2-back test group and the 0-back test group. On the other hand, in the 0-back test group, monotonousness and boredom VAS scores and sleepiness KSS score were significantly higher than those in the 2-back test group.

This indicates that the 30-minutes 0-back test is a monotonous, boring task with less stress, and the 30-minutes 2-back test is difficult and stressful task.

With the results illustrated above, the 30-minutes 0-back test is determined to be suitable as a task which causes fatigue due to monotonous work with low stress. In addition, the 30-minutes 2-back test is determined to be suitable as a task which causes fatigue due to difficult and stressful work.

Example 2

Potentiality Demonstration on Non-Invasive Fatigue Assessment (1) Experiment Design The inventors performed the 0-back test and the 2-back test on 10 healthy adults (male, age 30.8±9.4 (mean±standard deviation)) as the test subject for 30 minutes as tasks which causes mental fatigue. In the Example 1, it was determined that the 0-back test was appropriate as a monotonous task causing fatigue due to work with low stress, and the 2-back test was appropriate as a difficult task causing fatigue due to stressful work.

More specifically, an at-rest test, a visual stimulation test, and an audio stimulation test were performed as a before-task test. First, as an at-rest test, the subject was requested to stay still for two minutes in the open-eye state, and to stay still for another one minute in the closed-eye state. Subsequently, an optical stimulation to the left half of the subject's visual field was given using a blinking red light-emitting diode as the visual stimulation test. The stimulation was performed twice, each for one minute. The first blinking light was at 1 Hz, and the second blinking light was at 16 Hz.

Next, as the audio stimulation test, tone-burst stimuli (90 dB at 1000 Hz) is applied to the right ear, then to the left ear, for four minutes each. After the audio stimulation test, the 0-back test and the 2-back tests were performed for 30 minutes each.

After the N-back test, an after-task test was performed. The after-task test was the same as the before-task test, and tests were performed in the order of the at-rest test, the audio stimulation test, and the visual stimulation test. In addition, accelerated plethysmogram (APG), electrocardiogram (ECG), electroencephalogram (EEG), and magnetoencephalography (MEG) were continuously measured from the at-rest test before the task to the visual stimulation test after the task.

In addition, before and after the tasks, subjective tests were performed. The test includes measuring total fatigue, mental fatigue, physical fatigue, stress, motivation, sleepiness, difficulty, monotonousness, and boredom based on the Visual Analog Scale (VAS), and sleepiness based on Karolinska Sleepiness Scale (KSS).

Furthermore, in order to test the level of the subjects' chronic fatigue, the level of fatigue was measured by the Chalder fatigue scale only on the first day of the two tests. Furthermore, two tests were performed as a crossover to eliminate the influence of the order of the tests performed.

(2) Observation Points

APG test: a finger probe for fingertips (manufactured by NIHON KOHDEN CORPORATION) and a uniquely developed program for measuring accelerated plethysmogram were used for measurement. With this, the accelerated plethysmogram obtained by calculating the second order differential of fingertip plethysmogram is measured, and peak values of the a wave, b wave, c wave, d wave, and e wave. Subsequently, changes in the peak values of the accelerated plethysmogram waveform and the feature values using the accelerated plethysmogram along with the N-back test which is mental fatigue stress were analyzed. In addition, low frequency component (LF) and high frequency component (HF) were calculated by frequency analysis on the time-series data of the a-a interval change which is an interval of the a wave between the pulse, based on the maximum entropy method, and analyzed the change in the autonomous nerve activity indexes. Furthermore, the difference in the response of the accelerated plethysmogram waveforms at the time of audio stimulations before and after the N-back test was analyzed.

ECG test: An active tracer (manufactured by Arm Electronics Co., Ltd) was used for measurement. With this, the heartbeat variability was measured, and LF and HF were calculated by performing frequency analysis by the maximum entropy method, and analyze the change in the autonomous nerve activity index along the N-back test which is the mental fatigue stress was analyzed.

EEG test: NEUROFAX EEG 1518 (manufactured by NIHON KOHDEN CORPORATION) was used for the measurement. As such, the time-series brain wave was obtained, and the frequency analysis based on the fast Fourier transform (FFT) was performed. With reference to the reports by Kaida (Non-Patent Literature: Kaida K et. al., Validation of Karolinska sleepiness scale against performance and EEG variables. Clinical Neurophysiology. 117: 1574-1581, 2006.), the analysis was made on F3, C3, and O1, according to the International 10-20 system. The frequency bands for analysis included the waveband (between 3 Hz and 8 Hz) and the $\alpha$ waveband (between 8 Hz and 13 Hz), and the $\beta$ waveband (between 13 Hz and 25 Hz), and the arithmetic sum of the power values was determined to the a total power value. Note that, the $\delta$ waveband (between 0 Hz and 3 Hz) was excluded from the analysis, in consideration of blinks in the open-eye state.

MEG test: an 160-channel helmet magnetoencephalography meter (MEG vision) (manufactured by Yokogawa Electric Corporation) was used for measurement. Using the device, spontaneous magnetic field activities in the at-rest open-eye state and in the at-rest closed-eye state before and after the N-back test, and a frequency analysis by the FFT was performed the spontaneous magnetic field activities. The subject of the autonomous brain activity was all of the 160 channels, and each frequency range was defined in the same manner as the EEG.

Note that, the paired t-test was performed for the comparison between the two groups. Pearson's correlation analysis was performed to determine the correlation between the two groups. P value of less than 0.05 was determined to indicate statistic significance.

(3) Results

Subjective data after the N-back tests, the 0-back tested group indicated significantly higher sleepiness, monotonousness, and boredom VAS scores, compared to the 2-back tested group. On the other hand, the 2-back tested group had a tendency of indicating significantly higher stress and difficulty VAS scores, compared to the 0-back tested group. It is assumed that the results ensure the reliability and validity of the experiment, since the results have the approximately same tendency as the results of Example 1.

Figure 16A:
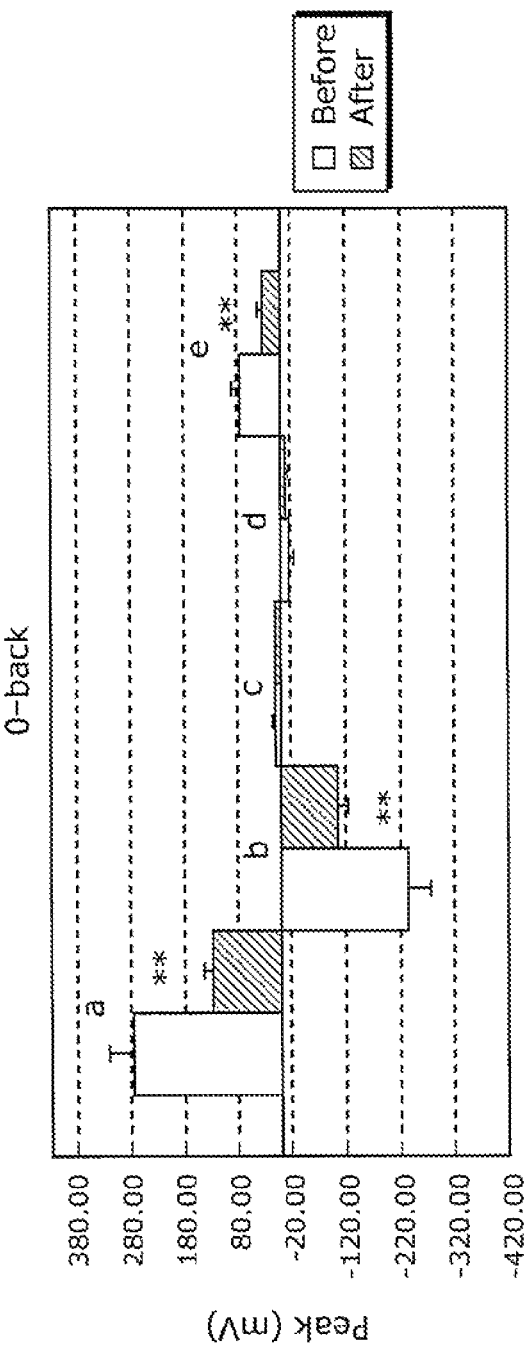
FIG. 16A illustrates a change in the peak value of APG waveforms before and after the mental fatigue stress (0-back).

FIG. 16A illustrates a change in the peak value of APG waveforms before and after the mental fatigue stress (0-back). FIG. 16A illustrates a change in the peak value of APG waveforms before and after the mental fatigue stress (2-back).

As illustrated in these diagrams, in the APG waveform analysis, as shown in earlier reports indicated by Patent Literature 1, the a wave and e wave significantly decreased and the b-wave significantly increased by the N-back test in both the 0-back tested group and the 2-back tested group. However, no influence of the mental fatigue stress was observed on the c wave and the d wave.

To put it differently, the c wave and the d wave are component waves that change due to factors other than fatigue. Thus, it is possible to cancel out the influence of the factors other than fatigue, by using the c wave or the d wave for the index value.

This phenomenon found in this experiment was assumed to be the feature common to fatigue, regardless of the fatigue due to monotonous work or difficult work. In view of this hypothesis, index values using the c wave or the d wave such as c/a, c/b, c/e, a−c, and c−a, and |d−c|/a are calculated, and the change in response to the mental fatigue stress was analyzed.

Figure 17:
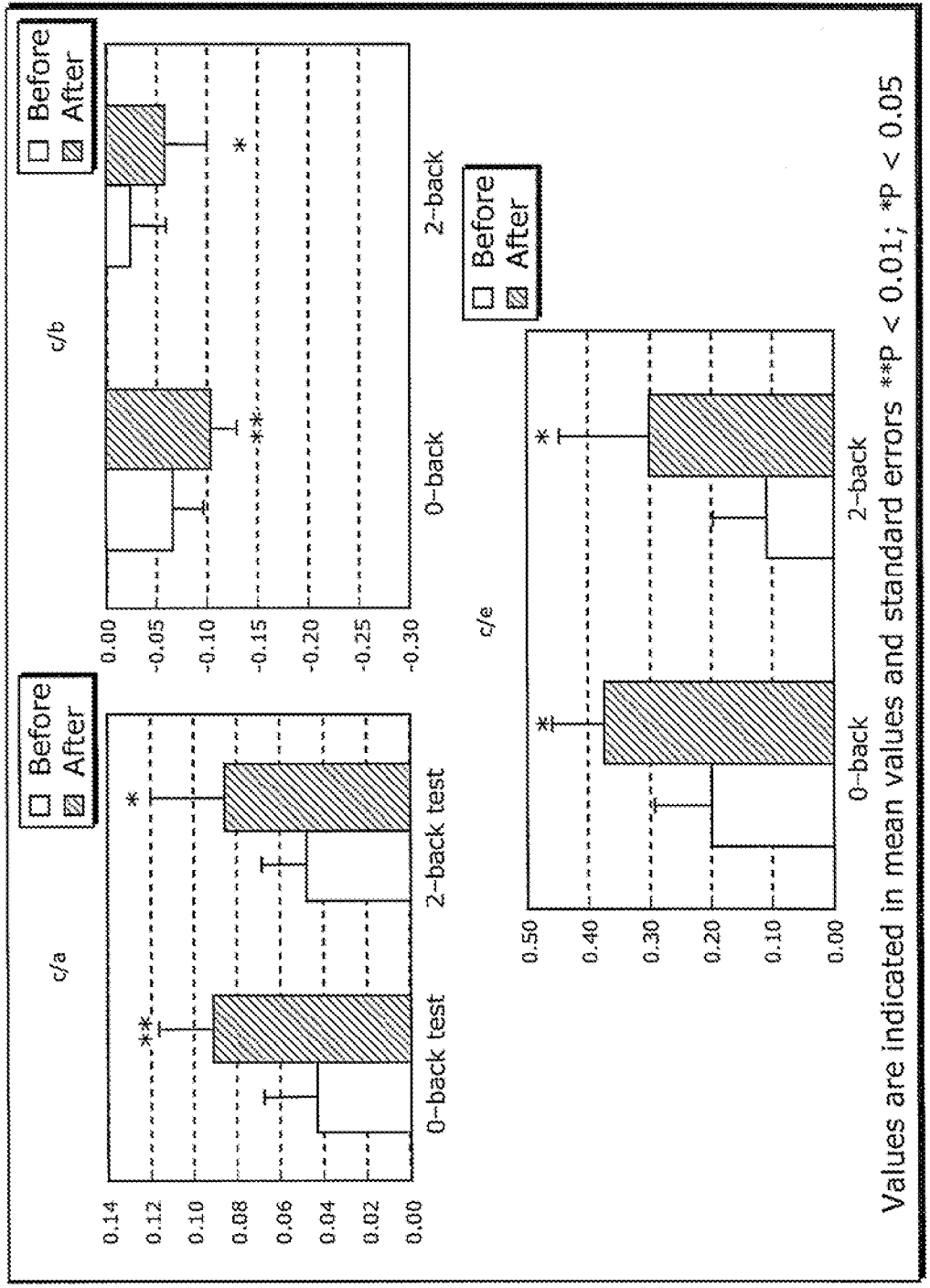
FIG. 17 illustrates changes in index values (c/a, c/b, c/e) based on APG before and after the mental fatigue stress.
Figure 18:
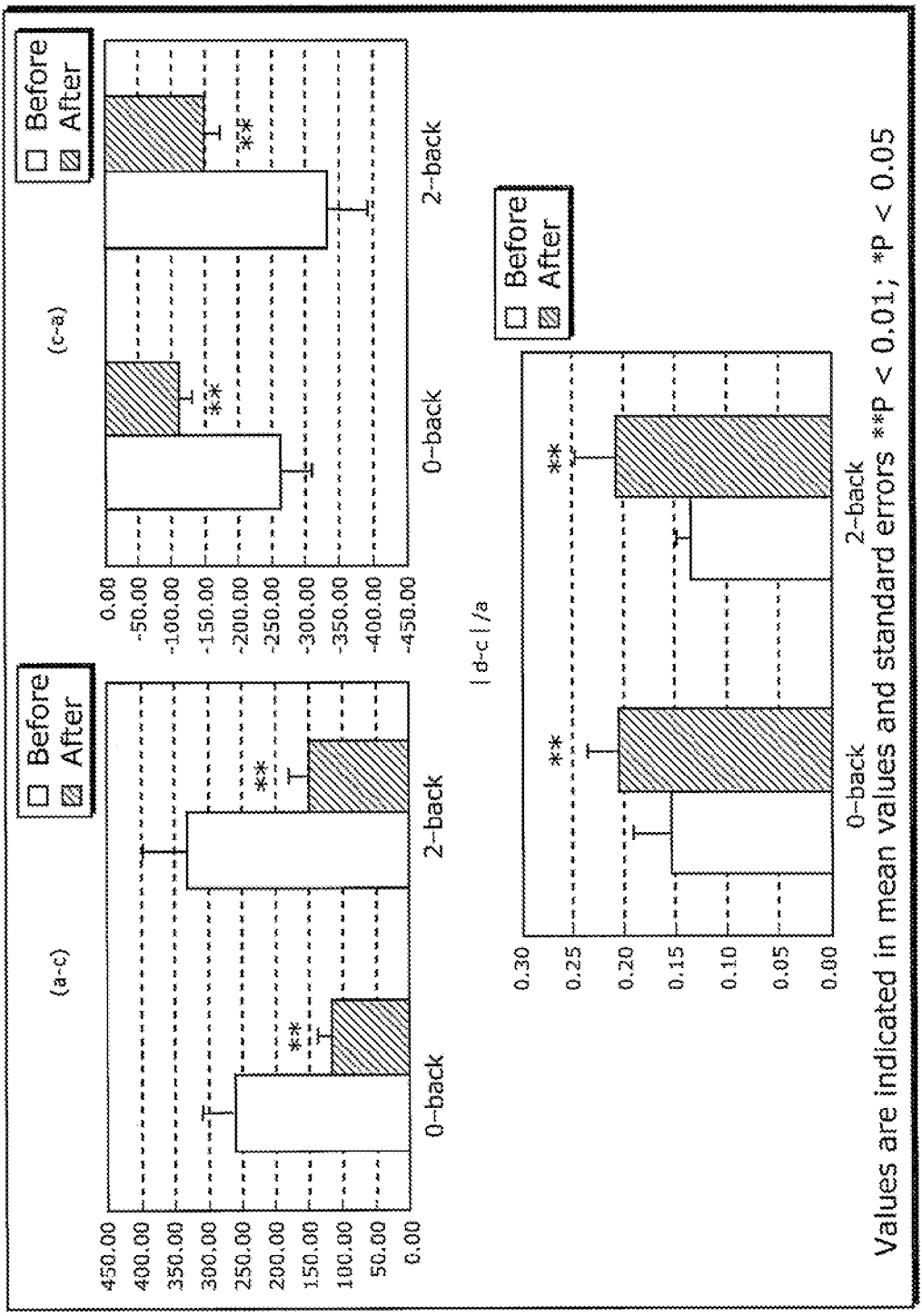
FIG. 18 illustrates changes in index values (a−c, c−a, |d−c|/a) based on APG before and after the mental fatigue stress.

FIG. 17 illustrates changes in index values (c/a, c/b, c/e) based on APG before and after the mental fatigue stress. FIG. 18 illustrates changes in index values (a−c, c−a, |d−c|/a) based on APG before and after the mental fatigue stress.

As illustrated in these diagrams, the analysis on the change in response to the mental fatigue stress indicated that c/a, c/e, c−a, |d−c|/a significantly increased, and c/b and a−c significantly decreased after the N-back test. For example, the c/a value illustrated in FIG. 17 significantly increased from 0.043 to 0.091 after the fatigue in the case of 0-back tested group, and significantly increased from 0.048 to 0.085 after the fatigue in the case of the 2-back tested group.

The index values using the c wave or the d wave which are not affected by the mental fatigue stress are capable of cancel out the influence of the factors other than fatigue, and were assumed to be more effective indexes for the fatigue assessment, compared to the case in which the peak values are used without any modification.

Figure 19:
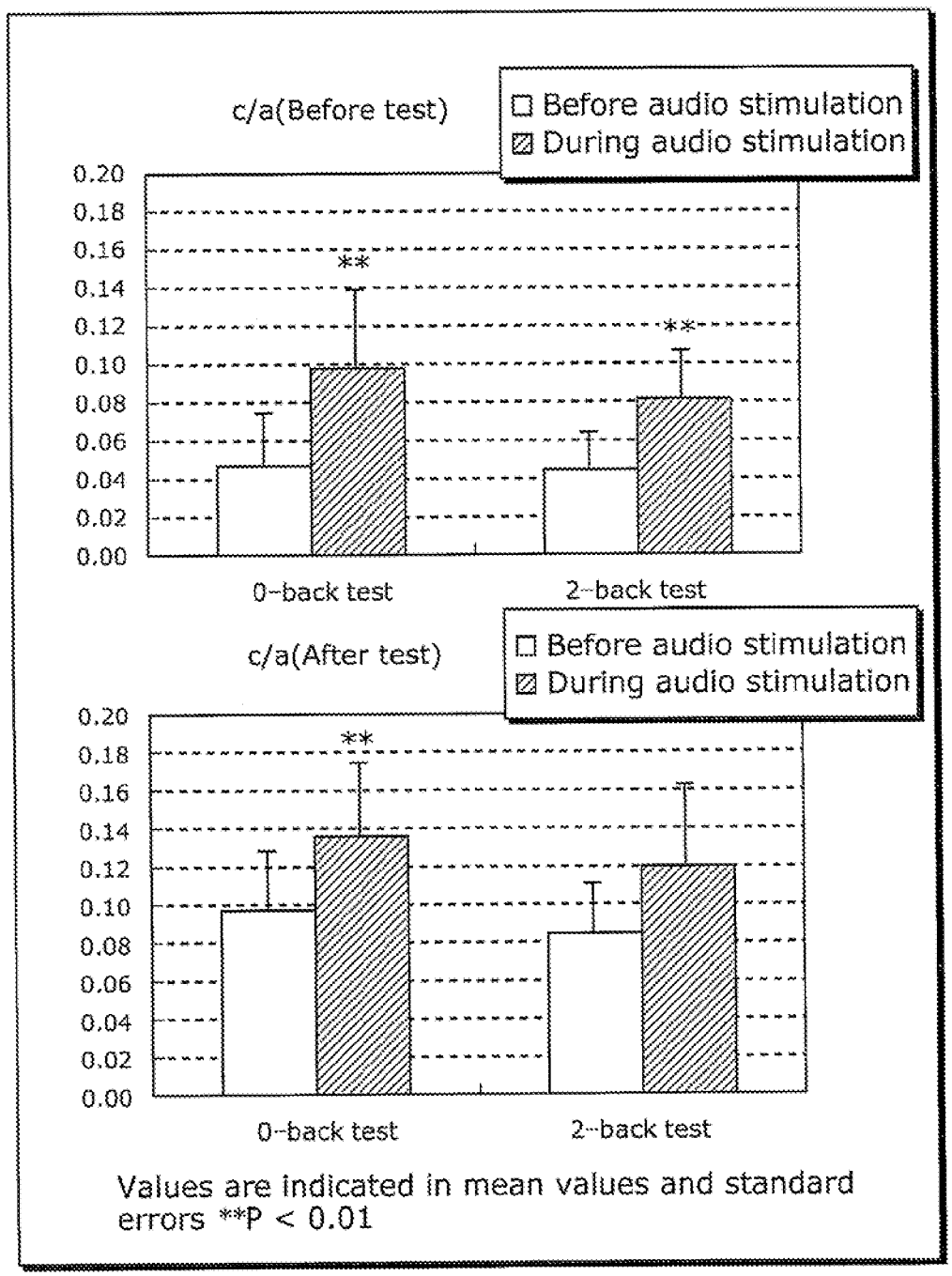
FIG. 19 illustrates changes in c/a values in response to audio stimulation before and after the mental fatigue stress.

FIG. 19 illustrates changes in c/a values in response to audio stimulation before and after the mental fatigue stress.

With regard to the reaction analysis of the APG waveform in response to the audio stimulation, the results of the analysis performed by the inventors indicated significant changes in c/a before and during the audio stimulation, before and after the 0-back test in the 0-back tested group. On the other hand, in the 2-back tested group, there was a significant change before and during the audio stimulation before the 2-back test. However, there was no significant change before and during the audio stimulation after the 2-back test (no "**" mark in the graph after the 2-back test).

This indicates that the 1% significance level was not satisfied before and during the audio stimulation after the 2-back test. More specifically, it indicates that the value was higher during the audio stimulation than before the audio stimulation with a probability less than 99%. Thus, it was assumed that the c/a in response to the audio stimulation behaves differently in the case of fatigue due to monotonous work and fatigue due to difficult work. The same results were obtained with index values other than c/a, such as, c/b, c/e, a−c, and c−a, and |d−c|/a.

Figure 20:
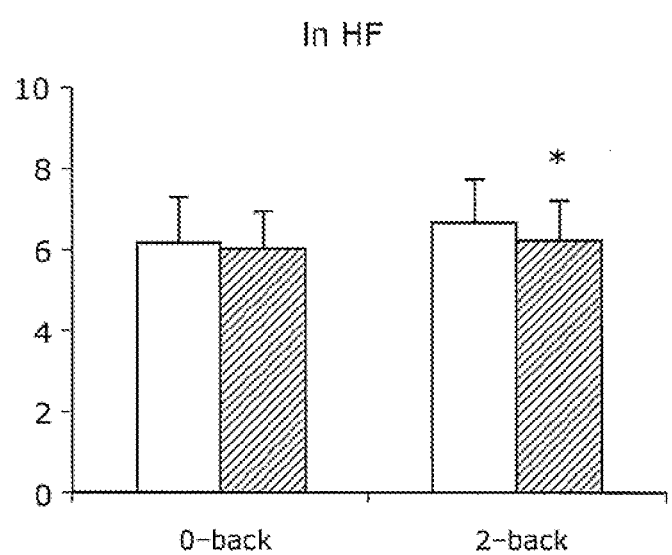
FIG. 20 illustrates changes in ln HF before and after the mental fatigue stress.

FIG. 20 illustrates changes in ln HF before and after the mental fatigue stress.

In the frequency analysis of the APG or the ECG, ln HF which is a logarithm of HF did not significantly change before and after the 0-back test in the 0-back tested group. However, in the 2-back tested group, ln HF significantly decreased after the 2-back test. More specifically, the ln HF illustrated in FIG. 20 decreased from 6.20 to 6.01 after the fatigue (no significant difference) in the 0-back tested group, and significantly decreased from 6.67 to 6.25 in the 2-back tested group after the fatigue.

Ln HF is assumed to be an index of parasympathetic nerve activity, and characteristic aspects of the results include that the fatigue due to monotonous work does not accompany a change in the parasympathetic nerve activity, and that the fatigue due to difficult work accompanies the decrease in the parasympathetic nerve activity.

Figure 21:
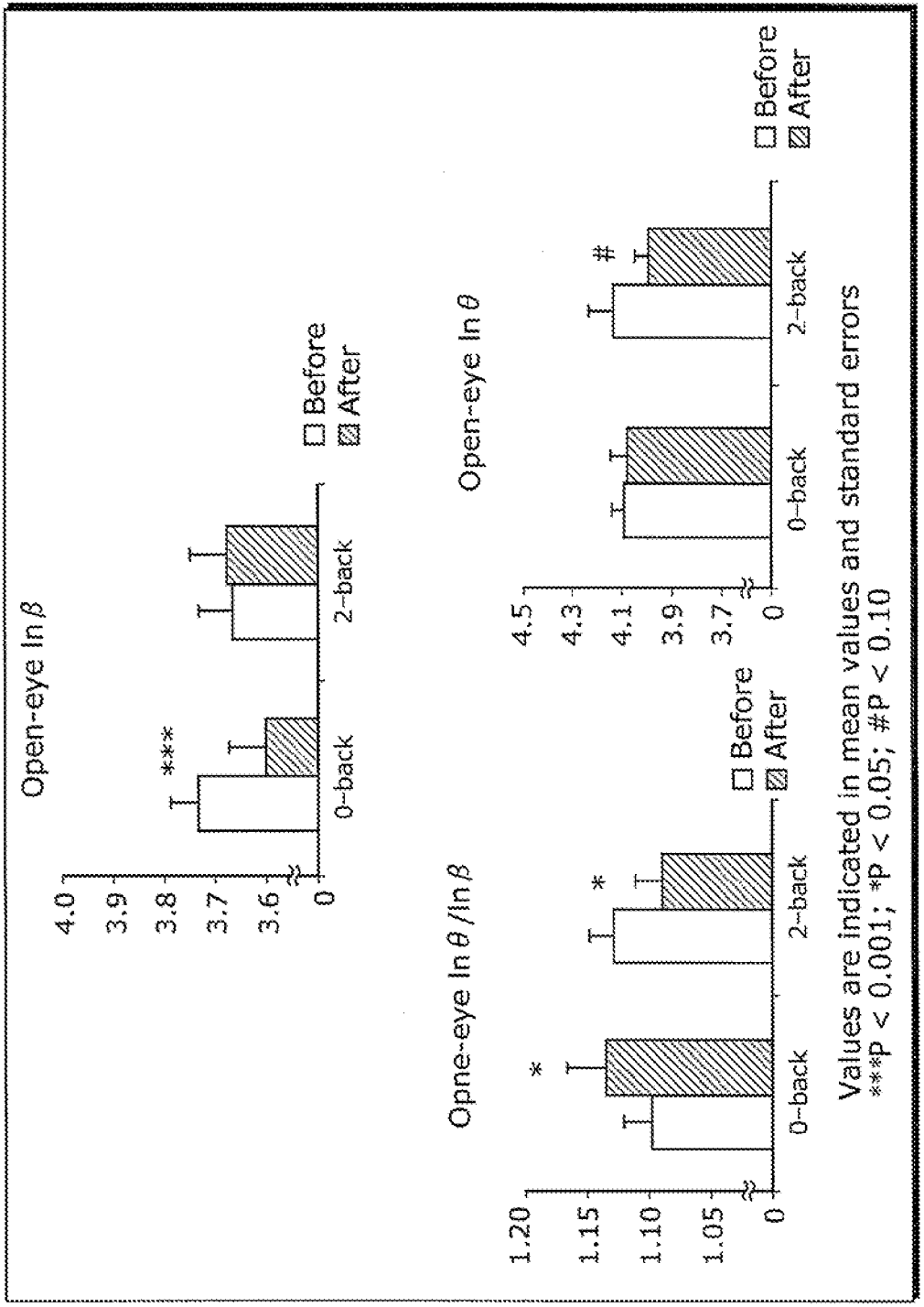
FIG. 21 illustrates changes in ln β, ln θ, and ln θ/ln β before and after the mental fatigue stress.

FIG. 21 illustrates changes in ln β, ln θ, and ln θ/ln β.

In the EEG frequency analysis in the at-rest open-eye state, ln β which is a logarithm of the power value of the β wave significantly decreased in the 0-back tested group after the 0-back test, and ln θ/ln β which is a Slow-wave Index significantly increased. In the 2-back tested group, ln θ and ln θ/ln β significantly decreased after the 2-back test.

Figure 22:
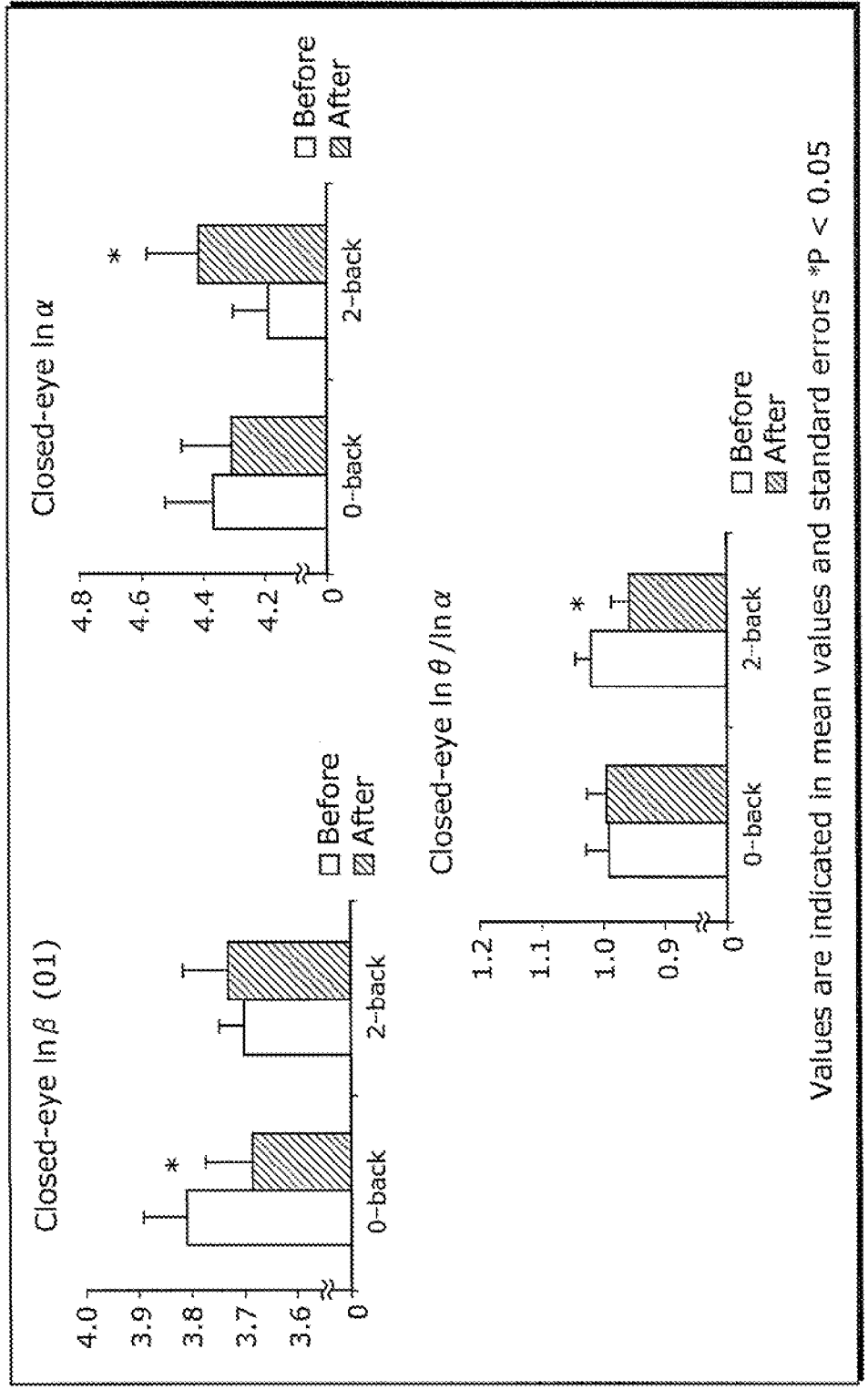
FIG. 22 illustrates changes in ln β, ln α, and ln θ/ln α before and after the mental fatigue stress.

FIG. 22 illustrates changes in ln β, ln α, and ln θ/ln α before and after the mental fatigue stress.

When the subject was at rest in closed-eye state, in the 0-back tested group, ln β at O1 significantly decreased after the 0-back test. In the 2-back tested group, ln α significantly increased after the 2-back test, and ln θ/ln α which is a slow-wave index in the closed-eye state significantly decreased.

With this, it is assumed that the fatigue due to monotonous work prompts the increase in the waves of lower frequency, inducing the decrease in the consciousness. On the other hand, it is assumed that the fatigue due to difficult work prompts the increase in the waves of higher frequency, inducing maintained or increased consciousness.

Figure 23A:
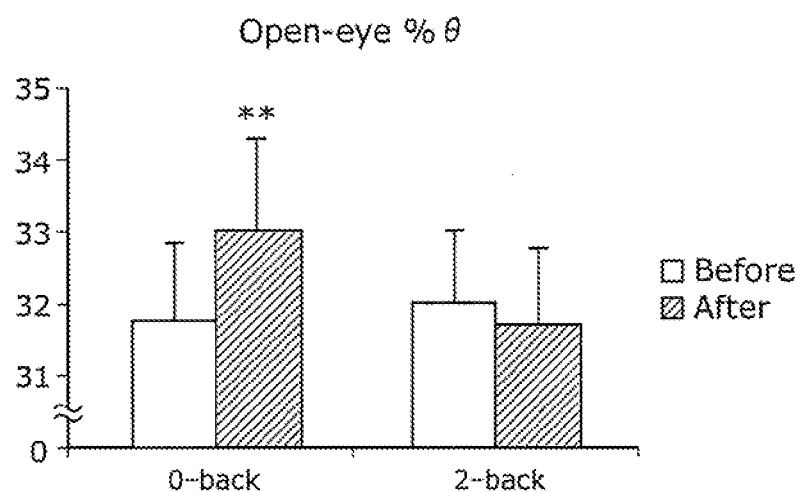
FIG. 23A illustrates changes in %θ before and after the mental fatigue stress.
Figure 23B:
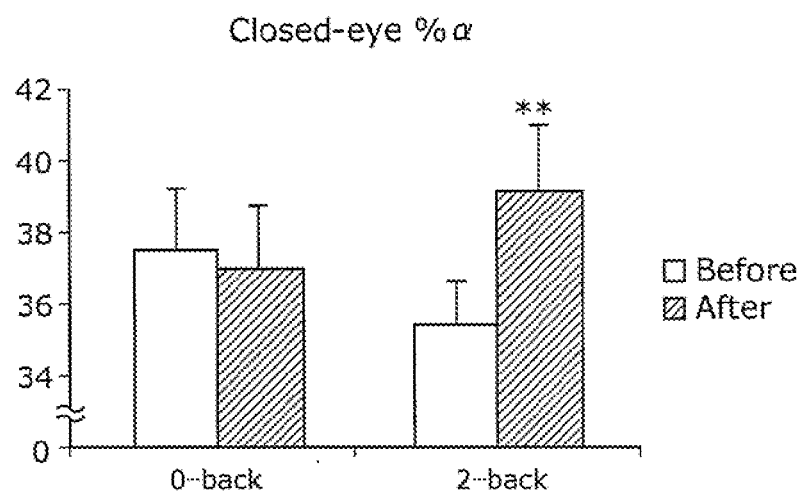
FIG. 23B illustrates changes in %α before and after the mental fatigue stress.
Figure 24:
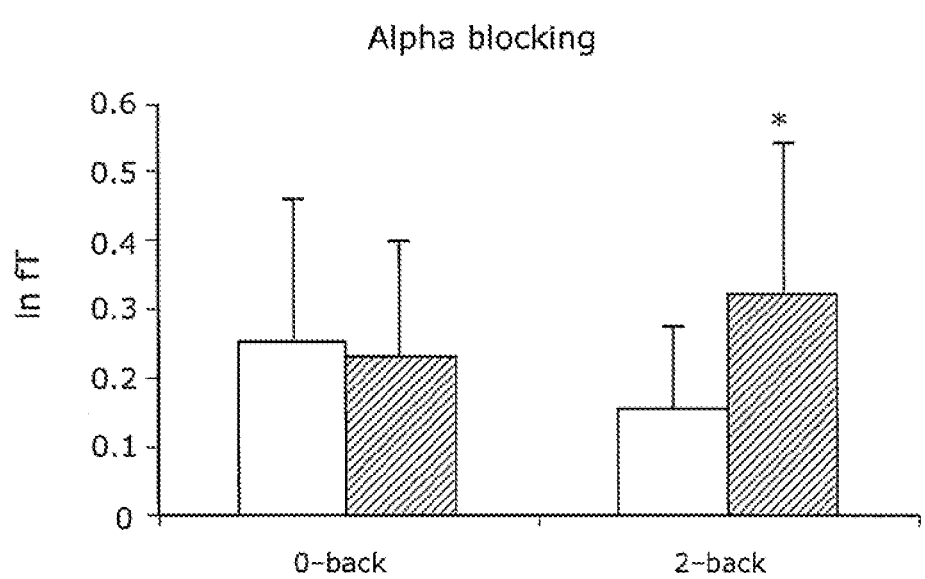
FIG. 24 illustrates changes in α-blocking before and after the mental fatigue stress.

FIG. 23A illustrates the change in % θ before and after the mental fatigue stress. FIG. 23B illustrates the change in % α before and after the mental fatigue stress. FIG. 24 illustrates changes in α-blocking before and after the mental fatigue stress.

As illustrated in FIG. 23A, in the 0-back tested group, a ratio (% θ) of the power value of the θ wave with respect to a total power value of the θ wave, the α wave, and the β wave significantly increased, when the subjects were at rest in the open-eye state after the 0-back test, in the frequency analysis of the MEG as well. Note that, the same result was observed in the power value of the θ wave, and the results match the increase in the lower frequency waves in the EEG.

In addition, as illustrated in FIG. 23B, when the subjects were at rest in the closed-eye state, in the 2-back tested group, a ratio (% α) of the power value of the α wave with respect to the total power value of the θ wave, α wave, and the β wave significantly increased after the 2-back test. Note that the same results were observed in the power value of the α wave and ln α.

Furthermore, as illustrated in FIG. 24, in the 2-back tested group, both α-blocking (closed eye−open eye) as a difference between the power values of the α wave when the subject was at rest in the open-eye state and when the subject was at rest in the closed-eye state, and α-blocking (closed eye/open eye) as a ratio of the power value of the α wave when the subject was at rest in the open-eye state to a power value of the α wave when the subject was at rest in the closed-eye state significantly increased. The same tendency was observed in the EEG as well.

Here, the mean frequencies in the power spectrums in the MEG and the EEG were calculated using a formula dividing a total sum of a multiplication of θ and the mean frequency of the θ waveband (5.5 Hz), a multiplication of α and the mean frequency of the α waveband (10.5 Hz), and a multiplication of β and the mean frequency of the β waveband (19 Hz) by the total power value. The result confirmed that the mean frequencies did not change before and after the 2-back test. With this, it is assumed that the fatigue due to difficult work not only prompts the increase in the wave with higher frequency, but also increases α wave which is one of the basic rhythms of the brain (increasing further, rather than turning back to the standard value).

With the results described above, the inventors found out that the c wave and the d wave in the APG waveform is less susceptible to the influence of the mental fatigue stress. With this, the inventors found out that using the index values using the c wave or the d wave improves the accuracy of the fatigue assessment compared to the conventional cases. Furthermore, the inventors found out that the parasympathetic nerve activity index calculated by the frequency analysis of the APG or the ECG and the power value of the α wave and the power value of the β wave calculated by the frequency analysis of the EEG or the MEG behave differently depending on the fatigue caused by monotonous work with low stress and fatigue caused by difficult work with high stress. Calculating the autonomous nerve activity index by the frequency analysis on the APG or the ECG, the increase in the sympathetic nerve activity and the decrease in the parasympathetic nerve activity at the time of fatigue have been known. However, the inventors found out that there is a type of fatigue which does not accompany the decrease in the parasympathetic nerve activity. Thus, the inventors found out that the difference in the type of fatigue can be distinguished by using the power value of the α wave and the power value of the β wave, not just determining whether or not the user is fatigued.

INDUSTRIAL APPLICABILITY

The human fatigue assessment device according to the present invention allows non-invasive and simple assessment of the human fatigue with high accuracy, and is effective for detecting fatigue early in daily lives. Furthermore, it allows the determination on the type of fatigue with a simple method and assistance on the user suitable for recovery, and thus it is applicable to a system for estimating the driver's condition in automobiles and to a system for managing employees in occupational fields.

REFERENCE SIGNS LIST 100, 400, 600, 1000, 1200 Human fatigue assessment device
101, 401 Physiological signal measuring unit
102, 402, 602, 1002, 1202 Feature value extracting unit
103, 403, 603, 1003, 1203 Storage unit
104, 1204 Fatigue determining unit
105, 405 Device controller
406, 606, 1006, 1206 Fatigue type determining unit
601 Checking unit
1001 Stimulation output unit
2501 Pulse wave measuring unit
2502 Accelerated plethysmogram calculating unit
2503, 2506 Storage unit
2504, 2507 Assessment unit
2505 Chaos analysis unit

The invention claimed is:

1. A human fatigue assessment device comprising:
a physiological signal measuring unit configured to measure a pulse wave signal of a user;
a feature value extracting unit configured to extract first feature values each of which is obtained from a systolic posterior component of the pulse wave signal measured by said physiological signal measuring unit;
a storage unit in which the first feature values extracted by said feature value extracting unit are stored; and
a fatigue determining unit configured to determine whether or not the user is fatigued, using the first feature values extracted by said feature value extracting unit,
wherein said fatigue determining unit is configured to compare a first feature value among the first feature values extracted by said feature value extracting unit and at least one of the first feature values stored in said storage unit, to determine whether or not the user is fatigued,
wherein said human fatigue assessment device further comprises
a checking unit configured to generate checking information for checking whether the user is in an open-eye state or in a closed-eye state,
wherein said physiological signal measuring unit is further configured to measure a brain signal of the user as a physiological signal, and to attach the checking information to the measured physiological signal,
wherein said feature value extracting unit is further configured to extract second feature values each of which (i) is obtained from the physiological signal measured by said physiological signal measuring unit and (ii) is related to at least one of (a) a power value in an α waveband in a time period during which the checking information indicates that the user is in the closed-eye state and (b) a power value in a β waveband in a time period during which the checking information indicates that the user is in the open-eve state or the closed-eye state,
wherein said storage unit stores the second feature values extracted by said feature value extracting unit, and
wherein said human fatigue assessment device further comprises
a fatigue type determining unit configured to determine, when said fatigue determining unit determines that the user is fatigued, a type of the fatigue of the user as to whether the fatigue is due to a first work or due to a second work that is more monotonous than the first work, by comparing a second feature value among the second feature values extracted by said feature value extracting unit and at least one of the second feature values stored in said storage unit.

2. The human fatigue assessment device according to claim 1,
wherein said feature value extracting unit is configured to calculate an accelerated plethysmogram from the pulse wave signal, and to extract the first feature values, using information on at least a c wave or a d wave which is a component wave of an accelerated plethysmogram corresponding to the systolic posterior component.

3. The human fatigue assessment device according to claim 2,
wherein said feature value extracting unit is configured to extract a ratio of a peak value of the c wave with respect to a peak value of an a wave, a b wave, or an e wave in the accelerated plethysmogram as the first feature value, and
wherein said fatigue determining unit is configured to determine that the user is fatigued, when absolute values of the first feature values increase in time-series.

4. The human fatigue assessment device according to claim 2,
wherein said feature value extracting unit is configured to extract a difference between peak values of the a wave and the c wave in the accelerated plethysmogram, and
wherein said fatigue determining unit is configured to determine that the user is fatigued when absolute values of the first feature values decrease in time-series.

5. The human fatigue assessment device according to claim 2,
wherein said feature value extracting unit is configured to extract a value obtained by dividing a difference between peak values of the c wave and the d wave in the accelerated plethysmogram by the a wave in the accelerated plethysmogram, and
wherein said fatigue determining unit is configured to determine that the user is fatigued when absolute values of the first feature values increase in time-series.

6. The human fatigue assessment device according to claim 1, further comprising
a device controller for controlling an external device which stimulates the user when said fatigue determining unit determines that the user is fatigued.

7. The human fatigue assessment device according to claim 1,
wherein when said feature value extracting unit extracts the second feature values as being related to a power value in the α waveband in a time period during which the checking information indicates that the user is in the closed-eye state, said fatigue type determining unit is configured to determine that the fatigue is due to the first work when the second feature values increase in time-series.

8. The human fatigue assessment device according to claim 1,
wherein when said feature value extracting unit extracts the second feature values as being related to a power value in a β waveband in a time period during which the checking information indicates that the user is in the open-eye state or the closed-eye state, said fatigue type determining unit is configured to determine that the fatigue is due to the second work when the second feature values decrease in time-series.

9. A human fatigue assessment method for assessing a fatigue of a living body by a computer, said method comprising:
measuring a pulse wave signal of a user;
extracting first feature values each of which is obtained from a systolic posterior component of the pulse wave signal measured in said measuring;
storing, in a storage unit, the first feature values extracted in said extracting; and
determining, using the computer, whether or not the user is fatigued, using the first feature values extracted in said extracting,
wherein, in said determining, a first feature value among the first feature values extracted in said extracting and at least one of the first feature values read from the storage unit among the first feature values stored in the storage unit are compared to determine whether or not the user is fatigued,
wherein said human fatigue assessment method further comprises
generating checking information for checking whether the user is in an open-eye state or in a closed-eye state,
wherein said measuring includes measuring a brain signal of the user as a physiological signal, and attaching the checking information to the measured physiological signal,
wherein said extracting includes extracting second feature values each of which (i) is obtained from the physiological signal and (ii) is related to at least one of (a) a power value in an α waveband in a time period during which the checking information indicates that the user is in the closed-eye state and (b) a power value in a β waveband in a time period during which the checking information indicates that the user is in the open-eye state or the closed-eye state,
wherein said human fatigue assessment method further comprises
storing, in the storage unit, the second feature values extracted in said extracting, and wherein said determining includes, when it is determined that the user is fatigued, determining a type of the fatigue of the user as to whether the fatigue is due to a first work or due to a second work that is more monotonous than the first work, by comparing a second feature value among the second feature values extracted in said extracting and at least one of the second feature values stored in the storage unit.

10. A program stored in a non-transitory computer readable recording medium, said program causing a computer to execute the human fatigue assessment method according to claim 9.

* * * * *